(12) United States Patent
Peterson

(10) Patent No.: US 9,532,961 B2
(45) Date of Patent: Jan. 3, 2017

(54) METHOD AND KIT FOR ADMINISTERING γ-GLUTAMYL-D-CYSTEINE FOR THE PREVENTION OF REPERFUSION INJURY FOLLOWING ISCHEMIC STROKE

(71) Applicant: Darryl R Peterson, Barrington Hills, IL (US)

(72) Inventor: Darryl R Peterson, Barrington Hills, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 13/868,902

(22) Filed: Apr. 23, 2013

(65) Prior Publication Data

US 2014/0024715 A1 Jan. 23, 2014
US 2016/0193167 A9 Jul. 7, 2016

Related U.S. Application Data

(60) Continuation-in-part of application No. 13/089,697, filed on Apr. 19, 2011, now Pat. No. 8,518,886, which is a division of application No. 11/479,776, filed on Jun. 30, 2006, now Pat. No. 7,956,037.

(60) Provisional application No. 61/638,177, filed on Apr. 25, 2012, provisional application No. 60/731,564, filed on Oct. 27, 2005, provisional application No. 60/696,404, filed on Jul. 1, 2005.

(51) Int. Cl.
*A61K 31/198* (2006.01)
*A61K 31/145* (2006.01)
*A61K 45/06* (2006.01)
*A61K 31/155* (2006.01)

(52) U.S. Cl.
CPC .......... *A61K 31/198* (2013.01); *A61K 31/145* (2013.01); *A61K 31/155* (2013.01); *A61K 45/06* (2013.01)

(58) Field of Classification Search
CPC .................................................. C07K 5/0215
See application file for complete search history.

(56) References Cited

U.S. PATENT DOCUMENTS 7,956,037 B2 6/2011 Peterson
8,518,886 B2 8/2013 Peterson

FOREIGN PATENT DOCUMENTS

WO 2004026118 A2 4/2004

OTHER PUBLICATIONS

Hamamoto et al. "Antimicrobial Activity and Stability to Proteolysis of Small Linear Cationic Peptides with D-Amino Acid Substitutions," Microbiol. Immunol., 46(11), 741-749, 2002.*
Bessalle et al. "All-D-magainin: chirality, antimicrobial activity and proteolytic resistance," FEBS, vol. 274, No. 1,2, Nov. 1990, pp. 151-155.*
Molhoek et al. "Improved proteolytic stability of chicken cathelicidin-2 derived peptides by d-amino acid substitutions and cyclization," Peptides 32 (2011) 875-880.*
Hong et al. "Effect of D-Amino Acid Substitution on the Stability, the Secondary Structure, and the Activity of Membrane-Active Peptide," Biochemical Pharmacology, vol. 58, pp. 1775-1780, 1999.*
Creighton "Proteins, Structure and Molecular Properties" 1993, p. 2.*
Novabiochem "Catalog and Peptide Synthesis Handbook" 1999, pp. x. xi, 1, 2, 18, 19.*
"Nomenclature Policy: Abbreviated Designations of Amino Acids", Am J Clin Nutr, 1988, 47, 589.*
Fields et al. "Solid phase peptide synthesis utilizing 9-fluorenylmethoxycarbonyl amino acids" Int. J. Peptide Protein Res 35, 1990, 161-214.*
Lazdunski, M., et al. "The Sodium/Hydrogen Exchange System in Cardiac Cells: Its Biochemical and Pharmacological Properties and its Role in Regulating Internal Concentrations of Sodium and Internal pH"; Mol. Cell Cardiol.; 17: 1029-1042, 1985.
Lee, W.-J., et al. "Role of oxoproline in the regulation of neutral amino acid transport across the blood-brain barrier"; J. Biol. Chem.; 271: 19129-19133, 1996.
Lee, W.-J., et al. "Glutamine transport by the blood-brain barrier: a possible mechanism for nitrogen removal"; Am. J. Physiol.; 274: C1101-C1107, 1998.
Lee, W.-J., et al. "Glucose transport by isolated plasma membranes of the blood-brain barrier"; Am. J. Physiol.; 272, 1997.
Masada, T., et al. "Attenuation of ischemic brain edema and cerebrovascular injury after ischemic preconditioning in the rat"; J. Cereb. Blood Flow Metab.; 21: 22-33, 2001.
Matsuda, T., et al. "SEA0400, a Novel and Selective Inhibitor of the Na+—Ca2+ Exchanger, Attenuates Reperfusion Injury in the in Vitro and in Vivo Cerebral Ischemic Models"; J. Pharmacol. Exp. Ther.; 298: 249-256, 2001.
Matsui, H., et al. "Increase in Na pump activity of brain-type isoforms via increased turnover rate after glutamate excitation of cerebral neurons"; In: "The sodium pump: structure mechanism, hormonal control and its role in disease"; edited by Schaner W. New York: Springer, 1994, pp. 710-713.
Matsumoto, S., et al. "Blockade of the mitochondrial permeability transition pore diminishes infarct size in the rat after middle cerebral artery occlusion"; J. Cereb. Blood Flow Metab.; 19: 736-741, 1999.
Mayer, B., et al. "Mitochondrial regulation of apoptosis"; NIPS; 18: 89-94, 2003.
Gruberg, L. "EXPEDITION: Sodium-Proton Exchange Inhibition to Prevent Coronary Events in Acute Cardiac Conditions Trial"; Medscape. Nov. 18, 2003. Retrieved from <http://www.medscape.com/viewarticle/464672_print>.
Meresse, S., et al. "Bovine brain endothelial cells express tight junctions and monoamine oxidase activity in long-term culture"; J. Neurochem.; 53: 1363-1371, 1989.

(Continued)

*Primary Examiner* — Christina Bradley
(74) *Attorney, Agent, or Firm* — Joseph A. Fuchs; Nixon Peabody LLP

(57) ABSTRACT

The present invention provides a method for preventing blood-brain barrier reperfusion injury in a mammalian blood-brain barrier endothelial cell during reperfusion following ischemic stroke comprising administering an effective amount of a γ-glutamyl-D-cysteine antioxidant to the subject and a kit for doing the same.

23 Claims, 18 Drawing Sheets

(56) References Cited

OTHER PUBLICATIONS

Morales, A., et al. "Characterization of a Na+—Ca2+ exchanger NCX1 isoform in bovine fasciculata cells of adrenal gland"; Mol. Cell Biochem.; 218: 41-45, 2001.
Muruganandam, A., et al. "Glutathione homeostasis and leukotriene-induced permeability in human blood-brain barrier endothelial cells subjected to in vitro ischemia"; Acta Neurochir. Suppl.; 76: 29-34, 2000.
Nakamura, A., et al. "Effects of KB-R7943, a novel Na+/Ca2+ inhibitor, on myocardial ischemia/reperfusion injury"; Folia Pharmacol. Jpn.; 111:105-115, 1998. (Partial English translation available).
Ogata, M., et al. "A novel and selective Na/Ca exchange inhibitor, SEA0400, improves ischemia/reperfusion-induced renal injury"; Eur. J. Pharmacol.; 478: 187-198, 2003.
Orrenius, S., et al. "Mechanisms of calcium-related cell death", Adv. Neurol.; 71: 137-151, 1996.
Peterson, D.R., et al. "Glutathione transport by the blood-brain barrier"; FASEB. J.; 13: A709, 1999.
Reese, T.S., et al. "Fine structural localization of a blood-brain barrier to exogenous peroxidase"; J. Cell Biol.; 34: 207-217, 1967.
Rosenberg, G.A. "Matrix metalloproteinases in neuroinflammation"; Glia; 39: 279-291, 2002.
Rosenberg, G.A., et al. "Matrix metalloproteinases and TIMPs are associated with blood-brain barrier opening after reperfusion in rat brain"; Stroke; 29: 2189-2195, 1998.
Rubin, L.L., et al. A cell culture model of the blood-brain barrier; J. Cell Biol.; 115: 1725-1735, 1991.
Sebastia, J., et al. "Evaluation of fluorescent dyes for measuring intracellular glutathione content in primary cultures of human neurons and neuroblastoma SH-SY5Y"; Cytometry; 51A: 16-25, 2003.
Skopicki, H.A., et al. "Low-affinity transport of pyroglutamyl-histidine in renal brush-border membrane vesicles"; Am. J. Physiol.; 257: C971-C975, 1989.
Sobolevsky, A.L., et al. "Blockade of NMDA channels in acutely isolated rat hippicampal neurons by the Na+/Ca2+ exchange inhibitor KB-R7943"; Neuropharmacology; 38: 1235-1242, 1999.
Todd, N.V., et al. "Reperfusion after cerebral ischaemia: influence of duration of ischaemia"; Stroke; 17: 460-466, 1986.
Tsukamoto, T., et al. Tight junction proteins form large complexes and associate with the cytoskeleton in an ATP depletion model for reversible junction assembly; J. Biol. Chem.; 272: 16133-16139, 1997.
Viravaidya, K., et al. "Development of a microscale cell culture analog to probe naphthalene toxicity"; Biotechnol. Prog.; 20: 316-323, 2004.
Welling, L.W., et al. "Physical properties of isolated perfused renal tubules and tubular basement membranes"; J. Clin. Invest.; 51: 1063-1075, 1972.
Wright, S.H., et al. "Stoichiometry of Na+-succinate cotransport in renal brush-border membranes"; J. Biol. Chem.; 257: 1773-1778, 1982.
Wulf, E., et al. "Fluorescent phallotoxin, a tool for the visualization of cellular actin"; Proc. Natl. Acad. Sci. USA; 76: 4498-4502, 1979.
Xu, M., et al. "Calcium preconditing inhibits mitochondrial permeability transition and apoptosis"; Am. J. Physiol.; 280: H899-H908, 2001.
Zhu, H.J., et al. "Glutamate up-regulates P-glycoprotein expression in rat brain microvessel endothelial cells by an NMDA receptor-mediated mechanism"; Life Sci.; 75: 1313-1322, 2004.
Neuwelt, E., et al. "Bone marrow chemoprotection without compromise of chemotherapy efficacy in a rat brain tumor model"; J. Pharmacol. Exp. Ther.; 309: 1-6, 2004.
Doolittle, N.D., et al. "Targeted delivery in primary and metastatic brain tumors"; Clin. Cancer Res.; 8: 1702-1709, 2002.
Eigel, B.N., et al. "Antisense inhibition of Na+/Ca2+ exchange during anoxia/reoxygenation in ventricular myocytes"; Am. J. Physiol.; 281: H2184-H2190, 2001.
Eigei, B.N., et al. "Na+/Ca2+ exchanger plays a key role in inducing apoptosis after hypoxia in cultured guinea pig ventricular myocytes"; Am. J. Physiol.; 287: H1466-H1475, 2004.
Riser, B.L., et al. "CCN genes and the kidney"; In: "CCN Proteins, A New Family of Cell Growth and Differentiation Regulators." Imperial College Press, London, 2005.
Peterson, D.R., et al. "Handling of angiotensin II and oxytocin by renal tubular segments perfused in vitro"; Am. J. Physiol.; 232: F319-F324, 1977.
Peterson, D.R., et al. "Effects of charge on membrane processing in the proximal nephron"; Am. J. Physiol.; 256: C304-C309, 1989.
Clapham, D.E. "TRP channels as cellular sensors"; Nature; 426: 517-524, 2003.
Fleig, A., et al. "The TRPM ion channel subfamily: molecular, biophysical and functional features"; Trends Pharmacol. Sci.; vol. 25, No. 12: 633-639, 2004.
Fonfria, E., et al. "TRPM2 channel opening in response to oxidative stress is dependent on activation of poly (ADP-ribose) polymerase"; Br. J. Pharmacol.; 143: pp. 186-192, 2004.
Harada, H., et al. "A novel method of detecting rCBF with laser-Doppler flowmetry without cranial window through the skull for a MCAO rat model"; Brain Research Protocols; 14: 165-170, 2005.
O'Brien, M.A., et al. "Poly(ADP-ribose) Polymerase Cleavage Monitored In Situ in Apoptotic Cells"; Biotechniques; vol. 30, No. 4: 886-891, Apr. 2001.
Sehirli, A.O., et al. "Protective effect of N-acetylcysteine on renal ischemia/reperfusion injury in the rat"; J. Nephrol.; vol. 16, No. 1: 75-80, 2003.
Plateel, et al. "Hypoxia increases the Susceptibility to Oxidant Stress and the Permeability of the Blood-Brain Barrier Endothelial Cell Monolayer"; Journal of Neurochemistry, vol. 65, No. 5, 1995; pp. 2138-2145; XP0000026578869; ISSN: 022-3042.
Bhattacharjee, et al. "The Effects of the Na+/Ca++ Exchange Blocker on Osmotic Blood-Brain Barrier Disruption," Brain Research, vol. 900, No. 2, May 11, 2001; pp. 157-162; XP000006257870; ISSN: 0006-8993.
Agarwal, R. et al. "Potential role of cerebral glutathione in the maintenance of blood-brain barrier integrity in rat." Neurochem. Res. 24:1507-1514; 1999.
Betz, A.L. "Transport of ions across the blood-brain barrier." Fed. Proc. vol. 45, No. 7; pp. 2050-2054. Jun. 1986.
Betz, A.L, et al. "Polarity of the blood-brain barrier: Distribution of enzymes between the luminal and antiluminal membranes of brain capillary endothelial cells." Brain Res. 192, pp. 17-28. Jul. 31, 1980.
Betz, A.L. et al. "Specialized properties and solute transport in brain capillaries." Ann. Rev. Physiol. 48:241-250. 1986.
Homma, M., et al. "High-affinity efflux transport system for glutathione conjugates on the luminal membrane of a mouse brain capillary endothelial cell line (MBEC4)." J. Pharmacol. Exp. Ther. 288:198-203. 1999.
Huai-Yun, H., et al. "Expression of multidrug resistance-associated protein (MRP) in brain microvessel endothelial cells." Biochem. Biophys. Res. Commun. 243:816-820. 1998.
Ishikawa, T. "The ATP-dependent glutathione S-conjugate export pump." Trends Biochem. Sci. 17:463-468. 1992.
Kannan, R., et al. "Evidence for carrier-mediated transport of glutathione across the blood-brain barrier in the rat." J. Clin. Invest. 85:2009-2013. Jun. 1990.
Kannan, R., et al. "Evidence for the existence of a sodium-dependent glutathione (GSH) transporter." J. Biol. Chem. vol. 271, No. 16, pp. 9754-9758. 1996.
Kannan, R., et al. "GSH transport in immortalized mouse brain endothelial cells: evidence for apical localization of a sodium-dependent GSH transporter." J. Neurochem. 73:390-399. 1999.
Keppler, D. et al. "Expression and localization of the conjugate export pump encoded by the MRP2 (cMRP/cMOAT) gene in liver." FASEB J. 11:509-516. Jun. 1997.
Kerper, L.E., et al. "Methylmercury efflux from brain capillary endothelial cells is modulated by intracellular glutathione but not ATP." Toxicol. Appl. Pharmacol. 141:526-531. 1996.
Kusuhara, H. et al. "The role of P-glycoprotein and canalicular multispecific organic anion transporter in the hepatobiliary excretion of drugs." J. Pharm. Sci. 87:1025-1040. Sep. 1998.

(56) References Cited

OTHER PUBLICATIONS

Kusuhara, H. et al. "Characterization of efflux transport of organic anions in a mouse brain capillary endothelial cell line." J. Pharmacol. Exp. Ther. 285:1260-65. 1998.

Lautier, D. et al. "Altered intracellular distribution of daunorubicin in immature myeloid leukemia cells." Int. J. Cancer 71:292-299. 1997.

Lee, W-J. et al. "Role of Oxoproline in the Regulation of Neutral Amino Acid Transport across the Blood-Brain Barrier." J. Biol. Chem. vol. 271, No. 32, pp. 19129-19133. 1996.

Loe, D.W. et al. "ATP-Dependent Transport of Aflatoxin B1 and Its Glutathione Conjugates by the Product of the Multidrug Resistance Protein (MRP) Gene." Mol. Pharmacol. 51:1034-1041. 1997.

Malo, C. et al. "Analysis of Kinetic Data in Transport Studies: New Insights from Kinetic Studies of Na+-D-Glucose Cotransport in Human Intestinal Brush-Border Membrane Vesicles Using a Fast Sampling, Rapid Filtration Apparatus." J. Membr. Biol. 122:127-141. 1991.

Mares, V. et al. "Up-regulation of gamma-glutamyl transpeptidase (GGT) activity in growth perturbed C6 astrocytes." Mol. Brain res. 136:75-80. 2005.

Meister, A. et al. "Glutathione." Ann. Rev. Biochem. 52, 711-760. 1983.

Mokrzan, E.M., et al., "Methylmercury-thiol uptake into cultured brain capillary endothelial cells on amino acid system." L. J. Pharm. Exp. Ther. 272, 1277-1284. 1995.

Oude Elferink, R.P.J., et al. "Hepatobiliary secretion of organic compounds, molecular mechanisms of membrane transport." Biochim. Biophys. Acta 1241, 215-268. 1995.

Peterson, D. et al. "isolation and behavior of plasma membrane vesicles made from cerebral capillary endothelial cells." In Pardridge, W. (ed.) Introduction to the Blood-Brain Barrier. Cambridge University Press, London, pp. 62-70. 1998. Partridge, et al. Introduction to the Blood-Brain Barrier, Methodology, Biology and Pathology, Cambridge University Press, 1998.

Peterson, D. et al. "Transport studies using membrane vesicles." In Nag, S. (ed.) The Blood-Brain Barrier. Springer Science & Business Media. Humana Press, Totowa, New Jersey; vol. 89, pp. 233-247. 2003.

Sanchez Del Pino, et al. "Neutral Amino Acid Transport by the Blood-Brain Barrier Membrane Vesicle Studies." The Journal of Biological Chemistry. vol. 267, No. 36, pp. 25951-25957. The American Society for Biochemistry and Molecular Biology, Inc. 1992.

Sanchez Del Pino, et al. "Biochemical Discrimination Between Luminal and Abluminal Enzyme and Transport Activities of the Blood-Brain Barrier." Journal of Biological Chemistry, vol. 270, No. 25, pp. 14907-14912, The American Society for Biochemistry and Molecular Biology, Inc. 1995a.

Sanchez Del Pino, et al. "Neutral Amino Acid Transport Characterization of Isolated Luminal and Abluminal Membranes of the Blood-Brain Barrier." Journal of Biological Chemistry, vol. 270, No. 25, pp. 14913-14918, The American Society for Biochemistry and Molecular Biology, Inc. 1995b.

Skopicki, H., et al. "Carrier-mediated transport of pyrryoglutamyl-histidine in renal brush border membrane vesicles." Am. J. Physiol., AJP—Cell Physiology, vol. 255, Issue 6 C822-C827, 1988. American Physiological Society.

Sun, D., et al. "Astroglial cell-induced expression of Na—K—Cl cotransporter in brain microvascular endothelial cells." Am. J. Physiol., AJP—Cell Physiology, vol. 269, Issue 6 C1506-C1512, 1995. American Physiological Society.

Yamazaki, M., et al. "Primary active transport of pravastatin across the liver canalicular membrane in normal and mutant *Eisai hyperbilirubinaemic* rats." Biopharm. Drug Dispos. 17:645-59. 1996.

Zhang, Y., et al., "Expression of various multidrug resistance-associated protein (MRP) homologues in brain microvessel endothelial cells," Brain Res.earch 876: (2000) 148-153, 2000. Elsevier Science B.V.

Zlokovic, B.V., et al, "Evidence for transcapillary transport of reduced glutathione in vascular perfused guinea-pig brain," Biochem Biophys Res Commun. May 1994 20130;201(1):401-408, 1994.

Lipton; "Ischemic Cell Death in Brain Neurons," Physiol. Rev., 1999; vol. 79, pp. 1431-1568.

Clark, et al. "Efficacy of Antioxidant Therapies in Transient Focal Ischemia in Mice," Stroke; 2001; 32:1000-1004.

Carroll, et al. "Nuclear factor-Nb activation during cerebral reperfusion: effect of attenuation with N-acetylcysteine treatment"; Mol. Brain Res. 1998; 56, pp. 186-191.

Khan, et al. "Administration of N-acetylcysteine After Focal Cerebral Ischemia Protects Brain Inflammation in a rat Model of Experimental Stroke"; J. Neurosci. Res., 2004; 76, 519-527.

Anderson, et al. "Glutathione Monoethyl Ester Provides Neuroprotection in a Rat Model of Stroke"; Neurosci. Lett, 2004; 354, 163-165.

Park, et al. "Dose-response Analysis of the Effect of 21-aminosteroid Tirilazad Mesylate (U-74006F) Upon Neurological Outcome and Ischemic Brain Damage in Permanent Focal Cerebral Ischemia"; Grain Res., 1994; 645, 157-163.

Xue, et al. "Tirilazad Reduces Cortical Infarction After Transient but not Permanent Focal Cerebral Ischemia in Rats"; Stroke, 1992; 23, 894-899.

Yu, et al. "Uric Acid Protects Neurons Against Excitotoxic and Metabolic Insults in Cell Culture, and Against Focal Ischemic Brain Injury In Vivo"; J. Neurosci. Res., 1998; 53, 613-625.

Kilic, et al. "Pinealectomy Aggravates and Melatonin Administration Attenuates Brain Damage in Focal Ischemia"; J. Cereb. Blood Flow Metab., 1999; 19, 511-516.

Pei, et al. "Pre-treatment with Melatonin Reduces Volume of Cerebral Infarction in a Permanent Middle Cerebral Artery Occlusion Stroke Model in the Rat"; Neurosci. Lett., 2002; 318, 141-144.

Kilic, et al. "Prophylactic Use of Melatonin Protects Against Focal Cerebral Ischemia in Mice: Role on Endothelin Converting Enzyme-1"; J. Pineal. Res., 2004; 37, 247-251.

Cao, et al. "alpha-Phenyl-tert-butyl-nitrone Reduce Cortical Infarct and Edema in Rats Subject to Focal Ischemia"; Brain Res., 1994; 644, 267-272.

Zhao, et al. "Delayed Treatment with the Spin Trap alpha-phenyl-N-tert-butyl Nitrone (PBN) reduces Infarct Size Following Transient Middle Cerebral Artery Occlusion in Rats"; Acta Physiol., Scand., 1994; 152, 349-350.

Schulz, et al. "Facilitation of Postischemic Reperfusion with alpha-PBN: Assessment using NMR and Doppler Flow Techniques"; Am. J. Physiol., 1997; 272, H1986-H1995.

Zausinger, et al. "Neurological Impairment in Rats After Transient Middle Cerebral Artery Occlusion: a Comparative Study Under Various Treatment Paradigms"; Brain Res., 200; 863, 94-105.

Yang, et al. "Neuroprotection by 2-h Postischemia Administration of Two Free Radical Scavengers, alpha-phenyl-n-tert-butyl-nitrone (PBN) and N-tert-butyl-(2-sulfophenyl)-nitrone (S-PBN), in Rats Subjected to Focal Embolic Cerebral Ischemia"; Experimental Nurology; 2000; 163, 39-45.

Kuroda, et al. "Neuroprotective Effects of a Novel Nitrone, NXY-059, After Transient Focal Cerebral Ischemia in the Rat"; J. Cereb. Bookd Flow Metab., 1999; 19, 778-787.

Sydserff, et al. "Effect of NXY-059 on Infarct Volume After Transient or Permanent Middle Cerebral Artery Occlusion in the Rat; Studies on Dose, Plasma Concentration and Therapeutic Time Window"; Br. J. Pharmacol., 2002; 135, 103-112.

Ginsberg, et al. "Stilbazulenyl Nitrone, a Novel Antioxidant, is Highly Neuroprotective in Focal Ischemia"; Ann. Neurol., 2003; 54, 330-342.

Van Der Worp, et al. "Dietary Vitamin E Levels Affect Outcome of Permanent Focal Cerebral Ischemia in Rats"; Stroke, 1998; 29, 1002-1006.

Mishima, et al. "Vitamin E Isoforms Alpha-tocotrienol and Gamma-tocopherol Prevent Cerebral Infarction in Mice"; Neurosci. Lett., 2003; 337, 56-60.

Garcia-Estrada, et al. "An alpha-lipoic acid-vitamin E Mixture reduces Postembolism Lipid Peroxidation, Cerebral Infarction, and Neurological Deficit i Rats"; Neurosci. Res., 2003; 47, 219-224.

(56) References Cited

OTHER PUBLICATIONS

Huang, et al. "Dehydroascorbic Acid, a Blood-Brain Barrier Transportable Form of Vitamin C, Mediates Potent Cerebroprotection in Experimental Stroke"; Proc. Natl. Acad. Sci. USA, 2001; 98, 11720-11724.

Takamatsu, et al. "Hydroxil Radical Generation After the Third Hour Following Ischemia Contributes to Brain Damage"; Eur. J. Pharmacol., 1998; 352, 165-169.

Sinha, et al. "Protective Effect of Resveratrol Against Oxidative Stress in Middle Cerebral Artery Occlusion Model of Stroke in Rats"; Life Sci., 2002; 71, 655-665.

Andrabi, et al. "Oxiresveratrol (trans-2,3',4,5'-tetrahydroxystilbene) is neuroprotective and inhibits the apoptotic cell death in transient cerebral ischemia"; Brain Res., 2004; 1017-, 98-107.

Mizuno, et al. "Inhibitory Effect of MCI-186, a Free Radical Scavenger on Cerebral Ischemia Following Rat Middle Cerebral Artery Occlusion"; Gen. Pharm., 1998; 30, 575-578.

Shichinohe, et al. "Neuroprotective Effects of the Free Radical Scavenger Edaravone (MCI-186) in Mice Permanent Focal Brain Ischemia"; Brain Res., 2004; 1029, 200-206.

The Edaravone Brain Infarction Study Group; "Effect of a Novel Free Radical Scavenger, Edaravone (MCI-186), on Acute Brain Infarction, Placebo-Controlled, Double-Blind Study at Multicenters"; Cerebrovasc. Dis., 2003; 15, 222-229.

Toyoda, et al. "Free Radical Scavenger, Edaravone, in Stroke with Internal Carotid Artery Occlusion"; J. Neurol. Sci., 2004; 221, 11-17.

Lee, et al. "Sequential Combination of Intravenous Recombinant Tissue Plasminogen Activator and Intra-Arterial Urokinase in Acute Ischemic Stroke"; Am. J. Neuroradiology, 2004; 25, 1470-1475.

Pilitsis, et al. "Inhibition of Na—(+)/Ca(2+) Exchange by KB-R7943, a Novel Selective Antagonist, Attenuates Phosphoethanolamine and Free Fatty Acid Efflux in Rat Cerebral Cortex During Ischemia-Reperfusion Injury"; Brain Res., 2001; 916, 192-198.

Medline Plus; "Antioxidants"; retrieved from <http://www.nlm.nih.gov/medlineplus/antioxidants.html> on Aug. 3, 2008; U.S. Natl. Library of Medicine, Bethesda, MD (3 pages).

Gilgun-Sherki, et al. "Antioxidant Therapy in Acute Nervous System Injury: Current State"; Pharm. Rev., 2002; 54, 271-284.

Drake, et al. "Elevation of Brain Glutathione by Gamma-glutamylcysteine Ethyl Ester Protects Against Peroxynitrite-induced Oxidative Stress"; J. Neurosci., 2002; 68, 776-784.

Yamamoto, et al. "Protective Actions of YM737, a new glutathione analog, against cerebral ischemia in rats"; Res. Commun. Chem. Pathol. Pharmacol., 1993; 81:221-232.

The National Institute of Neurological Disorders and Stroke rt-PA Stroke Study Group. "Tissue plasminogen activator for acute ischemic stroke." N. Engl. J. Med. 333: 1581-1587, 1995.

Abbruscato, T.J., et al. "Combination of hypoxia/aglycemia compromises in vitro blood-brain barrier integrity." J. Pharmacol. Exp. Ther.; 289: 668-675, 1999.

Anderson, M.E. "Glutathione and glutathione delivery compounds." In: "Advances in Pharmacology." New York: Academic Press, 1997, p. 65-78.

Audus, K.L., et al. "Brain microvessel endothelial cell culture systems." In: "Introduction to the Blood-Brain Barrier," edited by Pardridge WM. Cambridge: Cambridge University Press, 1998, p. 86-93.

Beuckmann, C.T., et al. "Tissue culture of brain endothelial cells—induction of blood-brain barrier properties by brain factors." In: "Introduction to the blood-brain barrier," edited by Pardridge WM. Cambridge: Cambridge University Press, 1998, p. 79-85.

Boado, R.J., et al. "A one-step procedure for isolation of poly(A)+ mRNA from isolated brain capillaries and endothelial cells in culture." J. Neurosci.; 57: 2136-2139, 1991.

Bradbury, M. "The Concept of a Blood-Brain Barrier." New York: John Wiley and Sons, 1979.

Bradbury, M.W.B. "The blood-brain barrier. Transport across the cerebral endothelium"; Circ. Res.; 57: 213-222, 1985.

Choudhri, T., et al. "Use of spectrophotometric hemoglobin assay to objectively quantify intracerebral hemorrhage in mice"; Stroke; 28: 2296-2302, 1997.

Cook, B.S., et al. "Regulation of Bcl-2 Family Proteins During Development and in Response to Oxidative Stress in Cardiac Myocytes: Association with Changes in Mitochondrial Membrane Potential"; Circ. Res.; 85: 940-949, 1999.

Counillon, L., et al. "Pharmacological characterization of stably transfected Na+/H+ antiporter isoforms using amiloride analogs and a new inhibitor exhibiting anti-ischemic properties"; Mol. Pharmacol.; 44: 1041-1045, 1993.

DeBault, L.E. "Gamma-glutamyl transpeptidase induction mediated by glial foot process-to-endothelium contact in co-culture"; Brain Res.; 220: 432-435, 1981.

DeKeyser, J., et al. "Clinical trials with neuroprotective drugs in acute ischaemic stroke: are we doing the right thing?" Trends Neurosci.; 22: 535-540, 2001.

Del Zoppo, G.J., et al "Ischaemic damage of brain microvessels: inherent risks for thrombolytic treatment in stroke"; J. Neurol Neurosurg. Psychiatry; 65: 1-9, 1998.

Dirnagl, U., et al. "Pathobiology of ischaemic stroke: an integrated view"; Trends Neurosci.; 22: 391-397, 1999.

Fukuhara, Y. et al. "Sodium-dependent succinate transport in renal outer cortical brush border membrane vesicles"; Am. J. Physiol.; 245: F374-F381, 1983.

Garay, R.P., et al. "The interaction of sodium and potassium with the sodium pumps in red cells"; J. Physiol. (London); 231: 297-325, 1973.

Gartshore, G., et al. "Influence of ischemia and reperfusion on the course of brain tissue swelling and blood-brain barrier permeability in a rodent of transient focal cerebral ischemia"; Exp. Neurol.; 147: 353-360, 1997.

Greene, E.L., et al. "Calcium and free radicals in hypoxia/reoxygenation injury of renal epithelial cells"; Am. J. Physiol.; 266: F13-F20, 1994.

Griffiths, E.J., et al. "Protective effects of low and high doses of cyclosporin A against reoxygenation injury in isolated rat cardiomyocytes are associated with differential effects on mitochondrial calcium levels"; Cell Calcium; 27: 87-95, 2000.

Halestrap, A.P. "The mitochondrial permeability transition: its molecular mechanism and role in reperfusion injury"; Biochem. Soc. Symp.; 66: 181-203, 1999.

Halestrap, A.P., et al. "Oxidative stress, thiol reagents, and membrane potential modulate the mitochondrial permeability transition by affecting nucleotide binding to the adenine nucleotide translocase": J. Biol. Chem.; 272: 3346-3354, 1997.

Hatashita, S. "Brain edema and cerebrovascular permeability during cerebral ischemia in rats"; Stroke; 21: 582-588, 1990.

Ikeda, K., et al. "The role of calcium ion in anoxia/reoxygenation damage of cultured brain capillary endothelial cells"; Acta Neuochir. Suppl. (Wien) 70:4-7, 1997.

Iwamoto, T., et al. "A novel isothiourea derivative selectively inhibits the reverse mode of Na+/Ca++ exchange in cells expressing NCX1"; J. Biol. Chem.; 271: 22391-22397, 1996.

Karaki, H., et al. "Calcium movement, distribution, and functions in smooth muscle"; Pharmacol. Rev.; 49: 157-230, 1997.

Karmazyn, M., et al. "The myocardial Na/H exchanger"; Drugs; 61: 375-389,2001.

Kuro, T., et al. "Protective Effect of KB-R7943, a novel Na+/Ca++ Exchange Inhibitor, on Ischemic Acute Renal Failure in Rats"; J. Pharmacol.; 81: 247-251; 1999.

Kuroiwa, T., et al. "Blood-brain barrier disruption and exacerbation of ischemic brain edema after restoration of blood flow in experimental focal cerebral ischemia"; Acta Neuropathol.; 76: 62-70, 1988.

Ladilov, Y., et al. "Cardioprotective effects of KB-R7943: a novel inhibitor of the reverse mode of Na+/Ca2+ exchanger"; Am. J. Physiol.; 276: H1868-H1876, 1999.

\* cited by examiner

FIG. 8
FIG. 8a
Stroke without drugs
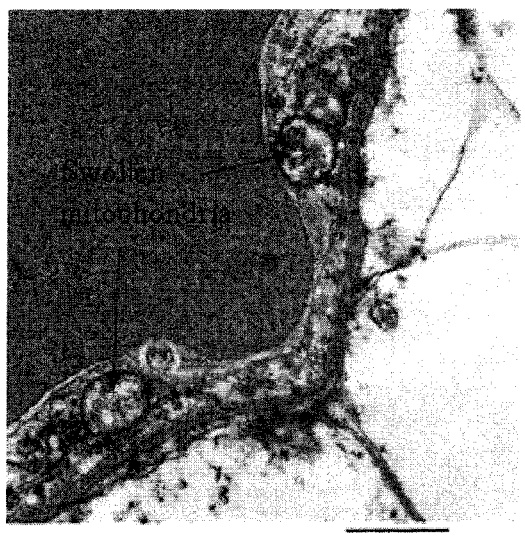
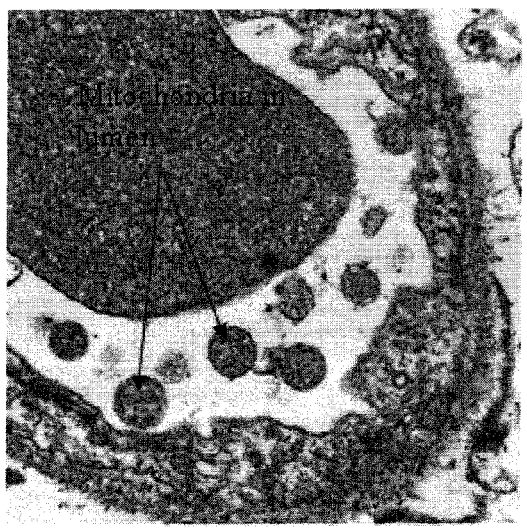
FIG. 8b
FIG. 8c
Stroke with drugs
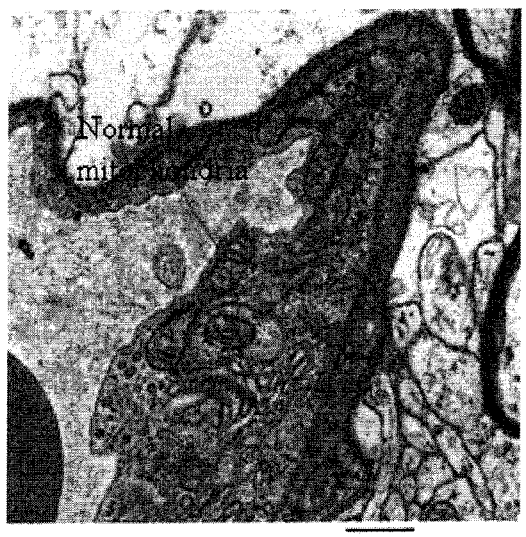
FIG. 8d

FIG. 9a
FIG. 9b
Stroke without drugs
Stroke with drugs
Infarction
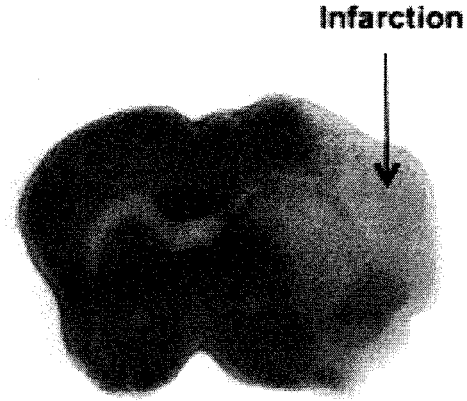
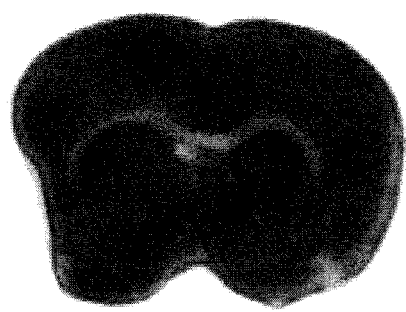

METHOD AND KIT FOR ADMINISTERING γ-GLUTAMYL-D-CYSTEINE FOR THE PREVENTION OF REPERFUSION INJURY FOLLOWING ISCHEMIC STROKE

CROSS-REFERENCE TO RELATED APPLICATION

This application claims priority to U.S. Provisional Patent Application Ser. No. 61/638,177, filed Apr. 25, 2012, and is a continuation-in-part of U.S. patent application Ser. No. 13/089,697, filed on Apr. 19, 2011, now U.S. Pat. No. 8,518,886, issued Aug. 27, 2013 which is a divisional of U.S. patent application Ser. No. 11/479,776, filed Jun. 30, 2006, now U.S. Pat. No. 7,956,037, issued Jun. 7, 2011, which claims priority from provisional applications Ser. No. 60/696,404, filed Jul. 1, 2005, and Ser. No. 60/731,564 filed Oct. 27, 2005, all of which are incorporated herein by reference and made a part hereof.

FEDERALLY SPONSORED RESEARCH OR DEVELOPMENT

This invention was made with United States government support under a Federal Work Study Program. The United States government has certain rights in the invention.

BACKGROUND OF THE INVENTION

Field of the Invention

The present invention relates generally to the use of γ-glutamyl-D-cysteine as a cytoprotective agent to prevent reperfusion injury of the blood-brain barrier that may contribute to hemorrhagic transformation due to thrombolysis following an ischemic stroke. The γ-glutamyl-D-cysteine can be used alone or used in combination with an agent that inhibits the reverse movement of Na/Ca exchange in the blood-brain barrier such as 2-[2-[4-(4-nitrobenzyloxy)phenyl]ethyl]isothiourea methanesulphonate (KB-R7943).

Background of the Invention

In the United States, someone experiences a stroke every minute, and dies from stroke-related complications approximately every three minutes. Strokes may be ischemic or hemorrhagic, but most are due to interrupted blood flow to the brain, resulting in hypoxia. Thus, the treatment for cerebral ischemia accompanying stroke includes therapies to re-establish blood flow. Surprisingly, reperfusion following cerebral ischemia may cause damage to cerebral capillaries (the blood-brain barrier, 63) that can precipitate cerebral edema and ensuing neuropathologies, and may contribute to cerebral bleeding termed hemorrhagic transformation (85, 86). Thus, the cure may actually augment the disease. This appears to be especially true if reperfusion is delayed several hours, and current practice is to avoid reperfusing a patient after approximately 3-4.5 hours of ischemia (1, 88). Recent evidence has verified that using tissue plasminogen activator (t-PA) to dissolve clots is an effective treatment for stroke, if administered within the three hour interval (1). Unfortunately, statistics reveal that 95% of stroke victims are not treated in time. Thus, it is clear that finding a way to prevent the potential side-effects associated with thrombolysis would be a significant and life-saving contribution. We have shown that γ-glutamyl cysteine is an antioxidant that contributes to inhibition of reperfusion injury of cerebral capillaries (U.S. Pat. No. 7,956,037). The present invention discloses the use of γ-glutamyl-D-cysteine to prevent reperfusion injury of the blood brain barrier that may contribute to hemorrhagic transformation due to thrombolytic treatment of ischemic stroke. γ-glutamyl-D-cysteine can be used alone or used in combination with an agent that inhibits the reverse movement of Na/Ca exchange in the blood-brain barrier such as 2-[2-[4-(4-nitrobenzyloxy)phenyl]ethyl]isothiourea methanesulphonate (KB-R7943).

These and other aspects and attributes of the present invention will be discussed with reference to the following drawings and accompanying specification.

SUMMARY OF THE INVENTION

An embodiment of the present invention is a method for preventing blood-brain barrier reperfusion injury in a mammalian blood-brain barrier endothelial cell during reperfusion following ischemic stroke comprising administering an effective amount of a γ-glutamyl-D-cysteine antioxidant to the subject. The surprising results of the present invention is that the γ-glutamyl-D-cysteine has shown to be more stable in the blood, and to have an equally as good antioxidant capacity as γ-glutamyl cysteine. The γ-glutamyl-D-cysteine antioxidant can be administered to a subject by intravenous injection into the subject. In an embodiment, the γ-glutamyl-D-cysteine is administered to the subject at a dose of about 400 mg/Kg. Preferably, the γ-glutamyl-D-cysteine is administered to the subject over a period of time. In another embodiment, the γ-glutamyl-D-cysteine is administered to the subject over a period of about one minute. In yet a further embodiment, the reperfusion following ischemic stroke is the result of a thrombolytic treatment, such as by administering tissue plasminogen activator or urokinase. In still another preferred embodiment, the method further comprises administering an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg.

Another embodiment of the present invention is a kit for use in preventing blood-brain barrier reperfusion injury in a mammalian blood-brain barrier endothelial cell during reperfusion following ischemic stroke. The kit includes a container of an effective amount of a γ-glutamyl-D-cysteine antioxidant. The kit may also contain include instructions for delivering the γ-glutamyl-D-cysteine by any suitable route of administration to a human subject including by intravenous injection including bolus injection or for delivery over a short time period such as one minute. In one preferred form of the invention the γ-glutamyl-D-cysteine will be in a powdered or lyophilized or other suitable form and the kit will include an acceptable diluent for reconstituting the γ-glutamyl-D-cysteine. An example of an effective amount is about 400 mg/Kg. In yet another preferred embodiment, the kit further includes a container of an agent that inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg. The KB-R7943 can be in the same or in a separate container from the γ-glutamyl-D-cysteine and can also be powdered or lyophilized or in other suitable form. The kit can be contained within packaging suitable for such medical products and may include other items such as syringes and needles and the like for delivering the components separately or together to a human subject.

Yet a further embodiment of the present invention is a method for preventing blood-brain barrier reperfusion injury in a mammalian blood-brain barrier endothelial cell during reperfusion following ischemic stroke comprising administering an effective amount of γ-glutamyl-D-cysteine and an agent that inhibits reverse movement of Na/Ca exchange in the blood-brain barrier to the subject, such as but is not limited to, 2-[2-[4-(4-nitrobenzyloxy)phenyl]ethyl]isothiourea methanesulphonate (KB-R7943). Preferably, the blood-brain barrier endothelial cell is a human cell.

BRIEF DESCRIPTION OF THE DRAWINGS

FIGS. 8a-8d are photomicrographs showing that cerebral capillary endothelial cells of rats exposed to ischemia and reperfusion in vivo are damaged, but that intravascular infusion of γ-Glu-Cys and KB-R7943 immediately prior to reperfusion prevents vascular damage. Rats were subjected to conditions of transient ischemic stroke using middle cerebral artery occlusion for 1 hour, followed by 24 hours of reperfusion. One group of stroked animals received cytoprotective drugs (i.e., KB-R 7943 [10 mg/Kg] and γ-Glu-Cys [400 mg/Kg]) intravascularly 1 min prior to reperfusion, and a second group of stroked animals were administered a placebo. Lateral cerebral cortical tissue was prepared for electron microscopy, and the cross-sectional area of mitochondria in blood-brain barrier endothelial cells was measured morphometrically. Two of four stroked animals without the drugs are shown in FIGS. 8a, 8b, and two of four stroked animals receiving the drugs are shown in FIGS. 8c, 8d. It is apparent that mitochondria are swollen in blood-brain barrier endothelial cells of stroked animals without the drugs (FIGS. 8a, 8b), suggesting the mitochondrial permeability transition. In some cases, damaged mitochondria have been extruded into the capillary lumen (FIGS. 8a, 8b, arrows). By contrast, the mitochondria of stroked animals given the drugs appear normal (FIGS. 8c, 8d). When compared to mitochondria of the unstroked contralateral hemisphere (internal control), the percent increase in cross-sectional area was significantly (P=0.0015) greater for the stroked animals not given the drugs (67±15 vs. 13±12, mean±SD, N=4 animals per group).

FIGS. 9a-9b are photomicrographs of coronal sections respectively from a representative stroked animal without administration of the drugs, and from a representative stroked animal with administration of the drugs, providing evidence that γ-Glu-Cys and KB-R7943 inhibit infarction in brain tissue of rats exposed to transient cerebral ischemia in vivo. Coronal sections were stained with 2,3,5-triphenyltetrazolium (TTC). FIG. 9a shows a coronal section from a stroked animal without the drugs, compared to that of a stroked animal administered the drugs, FIG. 9b. Unstained tissue observed in FIG. 9a indicates an area of infarction (arrow) in the stroked animal that was not given the drugs. The area of infarction for tissue from all 4 animals in both groups was quantified using morphometric measurements (Neurolucida), and was expressed as percent area of the stroked hemisphere. The data describing stroked animals without the drugs vs. stroked animals with the drugs, respectively, are as follows: 41.4±7.7 (mean±SE; N=4) vs. 17.3±12.2 (N=4). This difference approached significance (P=0.14) with only 4 animals in each group, and suggests that the drugs can have a general cytoprotective effect in the brain following transient ischemia.

FIG. 16a shows the antioxidant capacities of γ-Glu-Cys and γ-Glu-D-Cys at four concentrations (0.0625, 0.125, 0.3125 and 0.625 mM) were measured in the presence of rat serum (1-9%) in Tris Buffer. The 4 values for each of these 2 plots were standardized to uric acid equivalents (mM) for a common dose, averaged, and found not to be significantly different from each other. FIG. 16b shows the antioxidant capacities of γ-Glu-Cys and γ-Glu-D-Cys at varying concentrations (0.39-3.13 mM) in human plasma (90-99%), and the antioxidant capacities were measured as described above. The data show that a marginal difference was recorded at 0.39 mM, but a significant difference was not detected between the observed antioxidant capacities at concentrations of 0.78, 1.56, and 3.13 mM. Values are mean±SE. N=3 separate experiments for the 0.78, 1.56, and 3.13 mM concentrations. N=2 separate experiments for the 0.39 mM concentration. *P=0.047.

FIG. 17 shows that both γ-Glu-Cys (1 mM) and γ-Glu-D-Cys (1 mM) significantly inhibit spontaneous hemolysis, and that there is no significant difference in their cytoprotective effect in this assay. Furthermore, since neither peptide increased hemolysis, the data suggest that both drugs are not toxic under the experimental conditions. Values are mean±SE for 4 observations.

DETAILED DESCRIPTION OF THE INVENTION

Figure 1:
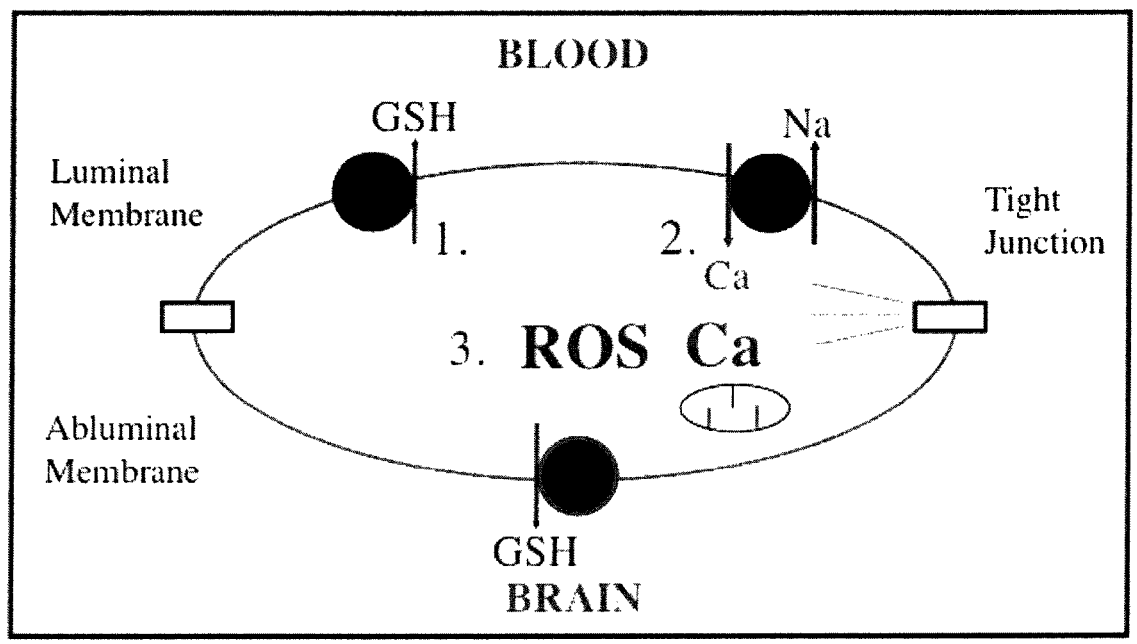
FIG. 1 is a schematic diagram showing a hypothetical model for ischemia-reperfusion damage to the blood-brain barrier. The numbers in the figure correspond to the sequence of events, as follows: 1) prolonged ischemia causes depletion of endogenous antioxidant (i.e., glutathione, GSH) via passive carriers on both the luminal (blood-facing) and abluminal (brain facing) plasma membranes of cerebral capillary endothelial cells; 2) reperfusion due to thrombolysis is associated with reverse movement of Na/Ca exchange at the luminal membrane, as well as the production of reactive oxygen species (ROS); 3) the presence of ROS and elevated calcium damages mitochondria and initiates apoptosis. Cell death reduces vascular integrity, and may lead to cerebral hemorrhage.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The present invention relates generally to the use of γ-glutamyl-D-cysteine as a cytoprotective agent to prevent reperfusion injury of the blood-brain barrier that may contribute to hemorrhagic transformation due to thrombolytic treatment of ischemic stroke. The surprising results of the present invention is the γ-glutamyl-D-cysteine has been shown to be more stable in the blood, and to have an equally as good antioxidant capacity as γ-glutamyl cysteine which itself is useful in the treatment of reperfusion injury. We propose that its analog γ-glutamyl-D-cysteine can be used alone, because of its cytoprotective properties, or in combination with an agent that inhibits the reverse movement of Na/Ca exchange in the blood-brain barrier. An example of such an agent is 2-[2-[4-(4-nitrobenzyloxy)phenyl]ethyl] isothiourea methanesulphonate (KB-R7943).

Another embodiment of the present invention is a kit for use in preventing blood-brain barrier reperfusion injury in a mammalian blood-brain barrier endothelial cell during reperfusion following ischemic stroke. The kit includes a container of an effective amount of a γ-glutamyl-D-cysteine antioxidant. The kit may also contain include instructions for delivering the γ-glutamyl-D-cysteine by any suitable route of administration to a human subject including by intravenous injection including bolus injection or for delivery over a short time period such as one minute. In one preferred form of the invention the γ-glutamyl-D-cysteine will be in a powdered or lyophilized or other suitable form and the kit will include an acceptable diluent for reconstituting the γ-glutamyl-D-cysteine. An example of an effective amount is about 400 mg/Kg. In yet another preferred embodiment, the kit further includes a container of an agent that inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg. The KB-R7943 can be in the same or in a separate container from the γ-glutamyl-D-cysteine and can also be powdered or lyophilized or in other suitable form. The kit may also include a container of tissue plasminogen activator such as t-PA or urokinase for delivery to a human subject after delivery of the γ-glutamyl-D-cysteine, or after the delivery of both γ-glutamyl-D-cysteine and KB-R7943. The kit can be contained within packaging suitable for such medical products and may include other items such as syringes and needles and the like for delivering the components separately or together to a human subject and the directions for the administration to a human subject.

A principal goal of treating cerebral ischemia associated with stroke is to re-establish blood flow to the brain (15). It is now clearly established that delayed reperfusion may cause further damage to the blood-brain barrier (19, 63, 85, 86), increasing complications and morbidity. Damage to the blood-brain barrier is characterized by an increase in its permeability to solutes (2), accompanied by fluid influx from blood-to-brain, cerebral edema (19, 30), and eventually hemorrhage if cell structure deteriorates (85, 86). Edema and hemorrhage, in turn, are associated with increased intracranial pressure and neural damage, possibly culminating in death.

Thus, the treatment for cerebral ischemia accompanying stroke includes therapies to re-establish blood flow, such as by administering tissue plasminogen activator (t-PA) or urokinase (1, 88). Surprisingly, reperfusion following cerebral ischemia may cause damage to the blood-brain barrier (63, 85, 86) that can precipitate cerebral edema and ensuing neuropathologies (19). Thus, the cure may actually augment the disease. This appears to be especially true if reperfusion is delayed several hours, and current practice is to avoid reperfusing a patient after approximately 3-4.5 hours of ischemia (1, 88).

Although relatively little is known about the mechanisms responsible for ischemia-reperfusion damage to the blood-brain barrier, it now appears that the process involves the following steps shown in FIG. 1: 1) prolonged ischemia causes depletion of endogenous antioxidant (i.e., glutathione, GSH) via passive carriers on both the luminal (blood-facing) and abluminal (brain facing) plasma membranes of cerebral capillary endothelial cells; 2) reperfusion due to thrombolysis is associated with reverse movement of Na/Ca exchange at the luminal membrane, as well as the production of reactive oxygen species (ROS); 3) the presence of ROS and elevated calcium damages mitochondria and initiates apoptosis. Cell death reduces vascular integrity, and may lead to cerebral hemorrhage. Hemorrhagic transformation is a complex condition that may involve pleiotropic mechanisms in addition to reperfusion injury (86). In general, a treatment to prevent brain damage following ischemic stroke has been elusive (87).

The blood-brain barrier is formed by polarized cerebral capillary endothelial cells that possess true tight junctions that impart a high electrical resistance (5, 51). Adjacent cell-types (i.e., astrocytes, neurons, pericytes) interact with the capillaries to form what is now termed the "neurovascular unit". Due to the presence of tight junctions, for substances to pass between the blood and brain they must cross the luminal (blood-facing) and abluminal (brain-facing) plasma membranes of the endothelial cells (8). Selectivity is provided by the presence of specific transport proteins in each membrane domain (9). The barrier becomes leaky to solutes, accompanied by unusually large fluid fluxes, when its integrity is compromised. This may occur with loosening of tight junctions (2), or more extensive cell damage (19, 63). We have shown that reperfusion injury to the blood-brain barrier is associated with an elevation of intracellular calcium, apparently due to reverse activation of the Na/Ca exchanger. This rise in intracellular calcium is accompanied by alterations of the cytoskeletal/tight junctional complex, increased permeability to sucrose, and mitochondrial changes indicative of apoptosis.

Based upon evidence in other cell systems, the mechanisms for ischemia-reperfusion injury to the blood-brain barrier are probably complex. In general, cellular damage associated with ischemia and reperfusion has been ascribed to a cascade of events (14) including: 1) production of toxic oxidative agents, 2) activation of enzymes which cause membrane damage, 3) abnormal behavior of the cytoskeleton, 4) up-regulation of inflammatory processes, and 5) damage to mitochondria. Interestingly, each of these processes has been associated with an elevation of intracellular calcium (14), which appears to play a key role in cellular injury. Our results show that reperfusion injury to the blood-brain barrier is associated with a rise in intracellular calcium that is reduced by pharmacologically inhibiting reverse activation of the Na/Ca exchanger. The data indicate that elevated calcium alters the cytoskeleton, resulting in increased permeability characteristics of tight junctions. Furthermore, compelling evidence demonstrates damage to mitochondria, resulting in activation of caspase 3. This is highly suggestive of apoptosis, and reveals an additional dimension of reperfusion injury to the blood-brain barrier.

Ischemic stroke has been characterized by two phases of injury to the blood-brain barrier (52, 53) that remain enigmatic. The early phase occurs within hours of re-establishing blood flow, and is typified by a modest, reversible increase in blood-brain barrier permeability and cerebral edema (52, 53). Following an apparent recovery, the second delayed effect may involve severe damage to the barrier, resulting in hemorrhagic transformation and death (52, 53, 85, 86). Based upon our data, we believe that the early phase is associated with a transient loosening of tight junctions in response to elevated intracellular calcium and alterations of the cytoskeleton. The second more devastating phase appears to coincide with mitochondrial damage and apoptosis. According to this interpretation, both phases are dependent upon the elevation of intracellular calcium that occurs during reperfusion, due to reverse activation of Na/Ca exchange. Thus, calcium is a central causative agent for injury, and each phase appears to be associated with the timing and compartmentalization of its respective calcium-dependent mechanisms.

Reperfusion injury associated with the cytoskeleton and tight junctions appears to include the following sequence of events: 1) binding of actin to a tight junctional protein, 2) contraction of actin and myosin in the presence of calcium, and 3) the production of stress conveyed to the junctional complex. We have shown that an alteration of the cytoskeleton in blood-brain barrier endothelial cells occurs during elevation of intracellular calcium, within the first 30 minutes of reperfusion. This is characterized by the formation of actin stress fibers, consistent with loosening of tight junctions (2). Furthermore, we have demonstrated that inhibition of calcium-activated myosin light chain kinase prevents this toxic effect. Myosin light chain kinase catalyzes the reaction between actin and myosin necessary for contraction. Since it has been shown that ischemia causes actin filaments to conjugate with ZO-1 (64), a tight junctional protein, force generated by contraction of the cytoskeleton would be expected to weaken tight junctions and facilitate the formation of stress fibers. Each of these observations is consistent with the interpretation that early reperfusion injury to the blood-brain barrier is associated with the cytoskeleton and tight junctions.

Ischemia-reperfusion injury has been associated in several cell types with an alteration of mitochondria termed the mitochondrial permeability transition (MPT). This occurs when ischemic events are accompanied by an elevation of intracellular calcium in the presence of reactive oxygen species (ROS), that induces a change in permeability characteristics of the inner mitochondrial membrane (22). This change in permeability is associated with release of cytochrome c, and results in uncoupling of oxidative phosphorylation. The reduction in ATP production initiates activation of caspases, including caspase 3, that has been associated with apoptosis (40). Apoptosis is a pattern of programmed cell death, characterized by a regular fragmentation of nuclear DNA that is measured by the so-called TUNEL assay. The apoptotic process results in cell damage, indicated by release of cytoplasmic lactate dehydrogenase (LDH). We have shown that activation of caspase 3 is delayed in blood-brain barrier cells exposed to ischemic conditions, occurring at 24 hours of reperfusion, but not after 3 hours of reperfusion. This pattern of delayed, potentially damaging toxicity is typical of what occurs during phase 2 of reperfusion injury to the blood-brain barrier.

It is known that ischemia-reperfusion injury to a variety of cell types involves an increase in intracellular calcium concentration (25) that serves as a signal to initiate a cascade of damaging effects (47). We hypothesized that the initial elevation of intracellular calcium concentration in the blood-brain barrier is associated with reverse movement of the Na/Ca exchanger during reperfusion, which effectively pumps calcium into the endothelial cells. Accordingly, this is stimulated by enhanced activity of the Na/H exchanger, which functions to remove hydrogen ions that accumulated during the ischemic phase, and reverses the electrochemical gradient for Na/Ca exchange by elevating intracellular sodium. The proposed sequence of events is as follows: 1) ischemia causes intracellular sodium concentration to increase, due to lowered ATP production and reduced activity of the sodium pump; 2) a diminished inwardly directed electrochemical gradient for sodium permits diminished Na/H exchange activity and thus causes an accumulation of hydrogen ions within the cells; 3) during reperfusion a large outwardly directed hydrogen ion gradient is created, driving the Na/H exchanger, which stimulates sodium uptake by the cells; 4) an elevated intracellular sodium concentration causes the Na/Ca exchanger to run in reverse, creating an unusually high level of intracellular calcium; 5) the increased level of calcium in metabolically re-activated cells (presence of ATP) causes pathological changes associated with abnormal permeability of the barrier, including disruption of the cytoskeleton and tight junctions, as well as damage to mitochondria.

Based on the above hypothesis, calcium-mediated injury to tight junctions and mitochondria in blood-brain barrier cells can be treated pharmacologically by preventing a rise in intracellular calcium during reperfusion, and/or replenishing antioxidant lost during ischemia. In the present invention, we disclose that providing antioxidants during ischemia/reperfusion assists in preventing the progression of mitochondrial injury to apoptosis. Effectively replenishing lost antioxidants at the time of reperfusion could serve as a reasonable therapeutic strategy. It has been shown that loss of GSH in the blood-brain barrier during ischemia is associated with injury (44). Since GSH synthesis requires energy, and carriers are present in blood-brain barrier cells allowing it to leave passively (50), one would expect GSH to become depleted during ischemia. GSH can be replenished by administering a glutathione-related antioxidant, such as but is not limited to glutathione (GSH), N-acetylcysteine (NAC), and a γ-glutamyl thiol such as γ-glutamylcysteine (γ-Glu-Cys) or its analog γ-glutamyl-D-cysteine which has been surprisingly shown in Example 10 below to be more stable in the blood, and to have an equally as good antioxidant capacity as γ-glutamyl cysteine, which itself is useful in the treatment of reperfusion injury. In addition, further prevention of reperfusion injury can be accomplished by co-administration of an agent that inhibits the reverse movement of Na/Ca exchange in the blood-brain barrier such as 2-[2-[4-(4-nitrobenzyloxy)phenyl]ethyl]isothiourea methanesulphonate (KB-R7943). What is meant by "co-administration" is that the administration of the agents can be simultaneous or in tandem in which one agent is administered followed by the other. Our data support the interpretation that γ-glutamyl antioxidants alone or in combination with an agent that inhibits the reverse movement of Na/Ca exchange in the blood-brain barrier, such as 2-[2-[4-(4-nitrobenzyloxy)phenyl]ethyl]isothiourea methanesulphonate (KB-R7943), prevent reperfusion injury of the blood-brain barrier endothelial cell following an ischemic stroke. Although the discovery of the use of these agents is based on the above-described hypothesis, the invention of the present disclosure should not be bound by any specific theory or hypothesis.

For in vivo administrations, the γ-glutamyl antioxidants can be injected intravenously at a dose of, for example, about 400 mg/Kg over 1 minute, immediately before reperfusion. However, of the glutathione-related antioxidants, GSH or NAC when infused intravenously may not be taken up by blood-brain endothelial cells quickly enough to completely restore intracellular GSH in a timely fashion. We have shown that a passive carrier is present in the luminal membrane of blood-brain barrier cells that normally facilitates cell-to-blood movement of GSH down its electrochemical gradient (50). With intracellular GSH depletion and relatively high levels of the antioxidant added to the blood, sufficient inward movement may be accomplished. Although NAC has been shown to function in a variety of cell types as a GSH precursor with cytoprotective effects (3), very little is known about its transport mechanisms by cells. Of concern is whether NAC must be deacetylated prior to uptake by blood-brain barrier cells. γ-glutamyl thiols like γ-glutamyl cysteine are potential cytoprotective agents under energy-depleted conditions, because they should enter passively and utilize less energy to form glutathione (3). Furthermore, since they possess sulfhydryl groups, they are antioxidants by themselves. Other similar cytoprotective antioxidants can also be used (e.g., γ-glutamyl-dipeptides containing a reactive sulfur such as γ-glutamyl-cystine, γ-glutamyl-methionine, γ-glutamyl-D-methionine and the like). Cytoprotective γ-glutamyl dipeptides containing a reactive sulfur can further be conjugated to other molecules such as NAC or another therapeutic agent.

These antioxidants can be administered alone, or more preferably, they can be administered in combination with an agent that inhibits the reverse movement of Na/Ca exchange in the blood-brain barrier. An example of such an agent is 2-[2-[4-(4-nitrobenzyloxy)phenyl]ethyl]isothiourea methanesulphonate (KB-R7943, by Pharmaceutical Research Laboratories, Kanebo Ltd., Osaka, Japan). Several studies in cardiac and renal tissues have shown that KB-R7943 inhibits Na/Ca exchange, and that it has a greater affinity for suppressing movement in the reverse direction (26). Furthermore, KB-R7943 has been shown to be cytoprotective under conditions of ischemia and reperfusion in both the heart and kidney (29, 45).

An embodiment of the present invention is a method for preventing blood-brain barrier reperfusion injury in a mammalian blood-brain barrier endothelial cell during reperfusion following ischemic stroke comprising administering an effective amount of a γ-glutamyl antioxidant to the subject. The blood-brain barrier endothelial cell is preferably a human cell. The γ-glutamyl antioxidant can be any antioxidant that is linked to a γ-glutamyl residue capable of reducing reactive oxygen species. A preferred γ-glutamyl antioxidant is γ-glutamyl cysteine and even more preferably γ-glutamyl-D-cysteine. Other suitable γ-glutamyl antioxidants may include but are not limited to γ-glutamyl cystine, γ-glutamyl methionine and γ-glutamyl-D-methione. The γ-glutamyl antioxidant can be administered to a subject by intravenous injection into the subject. In an embodiment, the γ-glutamyl antioxidant is administered to the subject at a dose of about 400 mg/Kg. Preferably, the γ-glutamyl antioxidant is administered to the subject over a period of time. In another embodiment, the γ-glutamyl antioxidant is administered to the subject over a period of about one minute. In yet a further embodiment, the reperfusion following ischemic stroke is the result of a thrombolytic treatment, such as by administering tissue plasminogen activator or urokinase. In still another preferred embodiment, the method further comprises administering an agent which inhibits reverse movement of Na/Ca exchange in the blood-brain barrier, such as but is not limited to 2-[2-[4-(4-nitrobenzyloxy) phenyl]ethyl]isothiourea methanesulphonate (KB-R7943). An example of an effective amount of KB-R7943 is 10 mg/Kg.

Yet a further embodiment of the present invention is a method for preventing blood-brain barrier reperfusion injury in a mammalian blood-brain barrier endothelial cell during reperfusion following ischemic stroke comprising administering an effective amount of γ-glutamyl cysteine, and even more preferably γ-glutamyl-D-cysteine and an agent that inhibits reverse movement of Na/Ca exchange in the blood-brain barrier to the subject, such as but is not limited to, 2-[2-[4-(4-nitrobenzyloxy)phenyl]ethyl]isothiourea methanesulphonate (KB-R7943). Preferably, the blood-brain barrier endothelial cell is a human cell.

EXAMPLES

Example 1

Culturing Blood-Brain Barrier Cells

Cultured blood-brain barrier cells can be used as an in vitro cellular model to confirm that Na/Ca exchange may operate in the reverse direction under conditions simulating reperfusion, following transient ischemia. Cerebral capillary endothelial cells are isolated from bovine brain by the method of Meresse et al. (42), or purchased from Cell Systems Corporation (Kirkland, Wash.). Cells are grown and maintained (up to passage 5) on collagen type I- and fibronectin-coated tissue culture flasks in Eagle's minimal essential medium supplemented with 10% fetal bovine serum (54, 62). To form a polarized endothelium, cells are seeded on cluster plate inserts and incubated in the presence of an astrocyte conditioned medium supplemented with cAMP, as previously described (4, 54). Endothelial cells may be identified by staining for factor VIII-related antigen, and the absence of a reaction product for glial fibrillary acidic protein. In addition, measurements of γ-glutamyl transpeptidase and electrical resistance (see below) may be made to indicate differentiation (13, 54). Several studies have shown that cultured brain capillary endothelial cells behave as a functional blood-brain barrier in vitro (6).

Example 2

Ischemia-Reperfusion Protocol Using Cultured Cells

Cultured blood-brain barrier cells can be exposed to conditions simulating ischemia and reperfusion, by a method similar to that reported in the literature (25). The precise composition of the incubation medium varies, depending upon the experimental protocols. In general, however, cells are incubated at 37° C. first in an ischemic medium (without glucose, pH 6.8) equilibrated with an atmosphere of 95% $N_2$ and 5% $CO_2$, followed by simulated reperfusion in a control medium (5.6 mM glucose, pH 7.4) equilibrated with room air and 5% $CO_2$. To provide a constant environment, the cells are maintained in sealed chambers (Billups-Rothenberg, Calif.) that have been pre-equilibrated to the desired atmospheric conditions during the course of the experiment.

Example 3

Evidence that Intracellular Sodium Concentration in Blood-Brain Barrier Endothelial Cells is Increased During Ischemia Cultured bovine blood-brain barrier endothelial cells were exposed to conditions simulating ischemia and reperfusion as described in Example 2. Sodium fluorescence is measured in cultured bovine blood-brain barrier endothelial cells under the following conditions: 1) control (120 minutes), 2) simulated ischemia (120 minutes), 3) simulated ischemia (90 minutes) followed by simulated reperfusion (30 minutes), 4) simulated ischemia/reperfusion (90/30 minutes), in the presence of an inhibitor (dimethylamiloride, 100 μM) of Na/H exchange.

Figure 3:
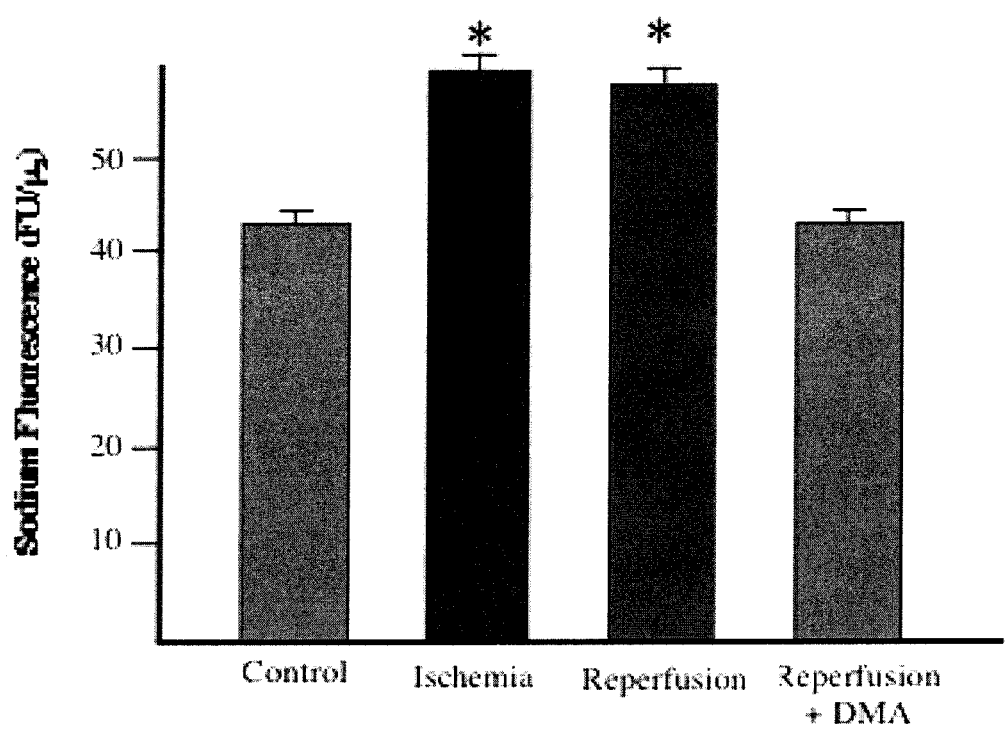
FIG. 3 is a bar graph of data showing that when cerebral capillary endothelial cells are exposed to ischemic conditions, intracellular sodium concentration increases and remains elevated during reperfusion; the elevation in intracellular sodium is prevented by pharmacological inhibition of the Na/H antiporter. Cultured bovine blood-brain barrier cells were exposed to conditions simulating ischemia and reperfusion, by incubating in 95% $N_2$/5% $CO_2$ without glucose (90 mins) at pH 6.8, followed by room air/5% $CO_2$ with 5.6 mM glucose (30 mins) at pH 7.4, respectively. Simulating ischemia-reperfusion in cultured blood-brain barrier endothelial cells resulted in a significant increase in intracellular sodium during the ischemic phase that was maintained during reperfusion. The rise in intracellular sodium observed during reperfusion was prevented by inhibiting Na/H exchange (100 μM dimethylamiloride, DMA). *$P<0.05$. Values are mean±SD. Measurements are made from 50 cells randomly chosen from 3 monolayers representing each treatment. Intracellular sodium was measured with fluorescent imaging, using sodium green.

The data, shown in FIG. 3, show that a significant (P<0.05) increase in intracellular sodium concentration is observed during ischemia, and remains elevated during reperfusion. Inhibition of Na/H exchange by 100 μM of dimethylamiloride (DMA) inhibits the rise in intracellular sodium observed following ischemia/reperfusion. Values are mean±SD. Measurements are made from 50 cells randomly chosen from 3 monolayers representing each treatment.

Example 4

Figure 4:
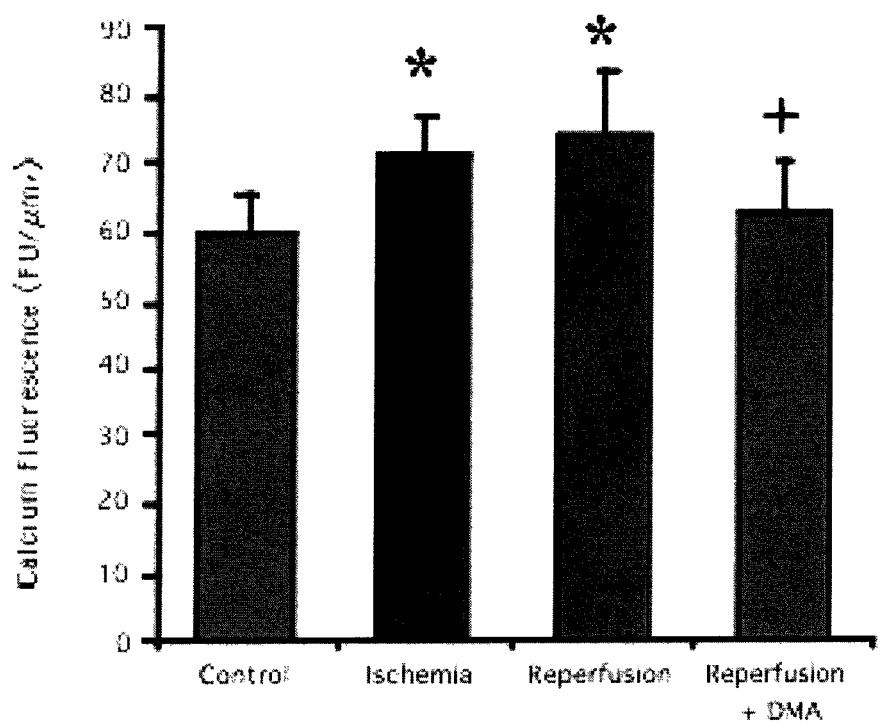
FIG. 4 is a bar graph of data showing that when cerebral capillary endothelial cells are exposed to ischemic conditions, intracellular calcium concentration increases and remains elevated during reperfusion; the elevation in intracellular calcium is prevented by pharmacological inhibition of the Na/H antiporter. Cultured bovine blood-brain barrier cells were treated as described above (FIG. 2). Simulating ischemia-reperfusion in cultured blood-brain barrier endothelial cells resulted in a significant increase in intracellular calcium during the ischemic phase that was maintained during reperfusion. The rise in intracellular calcium observed during reperfusion was prevented by inhibiting Na/H antiport (100 μM DMA). *$P<0.05$ compared to control. +$P<0.05$ compared to reperfusion. Values are mean±SD. Intracellular calcium was measured with fluorescent imaging, using Fluo-4.
Figure 5:
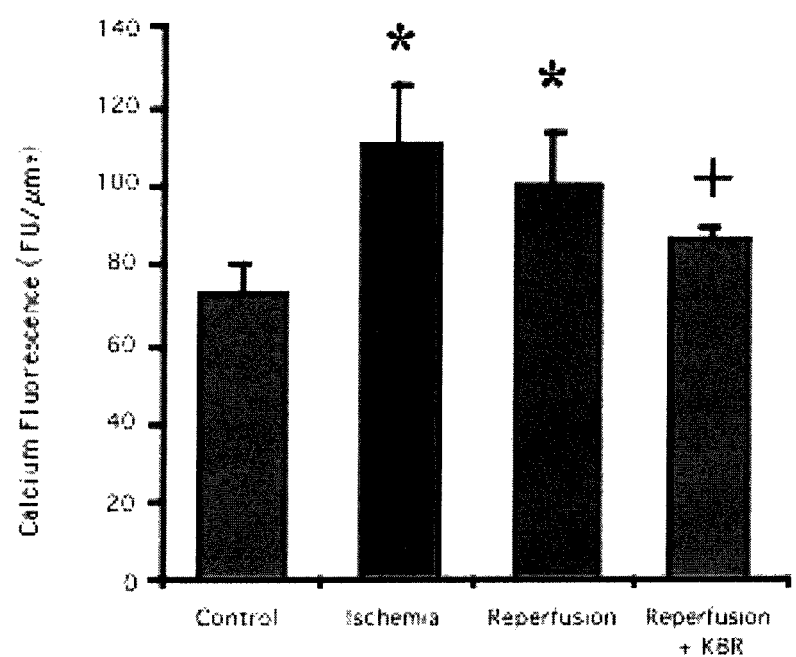
FIG. 5 is a bar graph of data showing that when cerebral capillary endothelial cells are exposed to ischemic conditions, intracellular calcium concentration increases and remains elevated during reperfusion; the elevation in intracellular calcium is prevented by pharmacological inhibition of reverse movement of the Na/Ca exchanger. Cultured bovine blood-brain barrier cells were treated as described above (FIG. 2). Simulating ischemia-reperfusion in cultured blood-brain barrier endothelial cells resulted in a significant increase in intracellular calcium during the ischemic phase that was maintained during reperfusion. The rise in intracellular calcium observed during reperfusion was prevented by inhibiting reverse movement of Na/Ca exchange (20 μM KB-R7943). *$P<0.05$ compared to control. +$P<0.05$ compared to reperfusion. Values are mean±SD. Intracellular calcium was measured with fluorescent imaging, using Fluo-4.

Evidence that Elevated Intracellular Sodium and Reverse Activation of Na/Ca Exchange Contribute to a Rise in Intracellular Calcium During Reperfusion, Following Ischemia Calcium fluorescence was measured in cultured bovine blood-brain barrier endothelial cells under the following conditions: 1) control, 2) simulated ischemia, 3) simulated ischemia followed by simulated reperfusion, 4) simulated ischemia/reperfusion, in the presence of an inhibitor (dimethylamiloride, 100 μM) of Na/H exchange (FIG. 4), or an inhibitor (KB-R 7943, 20 μM) of the reverse movement of Na/Ca exchange (FIG. 5). Intracellular calcium was quantified in cultured blood-brain barrier cells by using a fluorescent probe and confocal laser microscopy (25). Measurements were made under conditions of ischemia and reperfusion, as described in Example 2. For this protocol, the incubation medium was a bicarbonate buffer: (control) 114 mM NaCl, 81 mM $Na_2HPO_4$, 0.5 mM $MgCl_2$, 0.9 mM $CaCl_2$, 5.6 mM glucose, and 24 mM $NaHCO_3$, pH 7.4; (ischemic) 133.4 mM NaCl, 4.1 mM $Na_2HPO_4$, 4.1 mM $KH_2PO_4$, 12.6 mM Hepes, 2.4 mM Tris, 0.5 mM $MgCl_2$, 0.9 mM $CaCl_2$, and 6 mM $NaHCO_3$, pH 6.8. Prior to incubation, the media were sterile filtered and pre-equilibrated overnight in sealed chambers containing air plus 5% $CO_2$ (control) or 95% $N_2$ plus 5% $CO_2$ (ischemia). The next morning each chamber was re-gassed and placed in a water bath at room temperature for the duration of the experiment. The cells were preloaded for 30 minutes (25) with Fluo-4 (Molecular Probes), a fluorescent calcium probe. First, the growth medium was removed from the monolayers, after which they were washed with 2 ml sterile (control) bicarbonate buffer. Each dish was then treated with 2 ml of 5 μM sodium green in bicarbonate buffer with 0.1% dimethyl sulfoxide (DMSO), under an atmosphere of air plus 5% $CO_2$. Preloading with the calcium probe was done in the dark, since it is sensitive to light. Preloaded cells were washed with bicarbonate buffer and treated under conditions of ischemia and reperfusion, as described in Example 2. Following treatment, the tissue was excited at 494 nm, and fluorescence was measured at the same wavelength to determine bound calcium, since the probe is non-fluorescent when calcium is free. Calcium concentration was quantified in 80 randomly chosen (computer-assisted) cells, representing each treatment. Cells equilibrated with known amounts of calcium served as standards to quantify intracellular calcium levels (20).

The data, shown in FIG. 4, show that a significant (P<0.05) increase in intracellular calcium concentration is observed during ischemia, and remains elevated during reperfusion. Inhibition of Na/H exchange by 100 μM of DMA (FIG. 4) or the reverse movement of Na/Ca exchange by 20 μM of KB-R7943 (KBR) (FIG. 5) inhibits the rise in intracellular calcium observed following ischemia/reperfusion. Values are mean±SD for 80 observations. This supports the working hypothesis that activation of Na/H exchange and reverse movement of Na/Ca exchange during reperfusion following transient ischemia elevates intracellular calcium.

Example 5

Evidence that Activation of Na/H Exchange During Ischemia/Reperfusion Results in Elevated Intracellular Calcium Concentration that in Turn Initiates Mitochondrial Damage and Caspase 3 Activation Caspase 3 activity was measured in cultured bovine blood-brain barrier endothelial cells under control conditions (24.5 hours), simulated ischemia (24.5 hours), or ischemia (0.5 hours) followed by reperfusion (24 hours, I/Rep) as described in Example 2.

Figure 6:
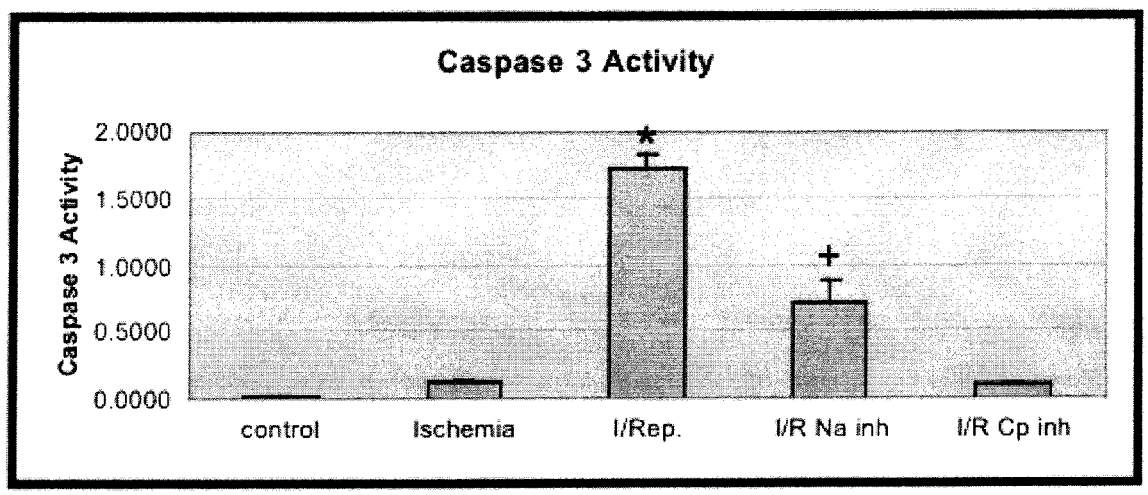
FIG. 6 is a bar graph of data showing that ischemia followed by reperfusion of cultured cerebral capillary endothelial cells results in an increase of caspase 3 activity that is inhibited by an inhibitor of Na/H exchange. Caspase 3 activity is expressed in cultured blood-brain barrier cells exposed to conditions simulating ischemia-reperfusion. Twenty-four hours of reperfusion following 30 mins of ischemia resulted in a large increase in caspase 3 activity that was inhibited with DMA (100 μM). *$P<0.05$ from control; +$P<0.05$ from I/Rep. I/Rep is ischemia plus reperfusion; I/R Na inh is ischemia-reperfusion with inhibitor; I/R Cp inh is ischemia-reperfusion with a specific caspase inhibitor. Values are mean±SD for 3 observations.

Ischemia followed by reperfusion results in a highly significant increase in caspase 3 activity (*, P<0.0001), that is inhibited (+, P<0.05) by incubating in the presence of an inhibitor (dimethylamiloride, 100 μM) of Na/H exchange. Values are mean±SD for 3 observations. The data, shown in FIG. 6, are consistent with the hypothesis that activation of Na/H exchange during ischemia/reperfusion results in elevated intracellular calcium concentration that in turn initiates mitochondrial damage and caspase 3 activation. Caspase 3 activation is associated with the mitochondrial pathway for programmed cell-death (apoptosis).

Example 6

Figure 2:
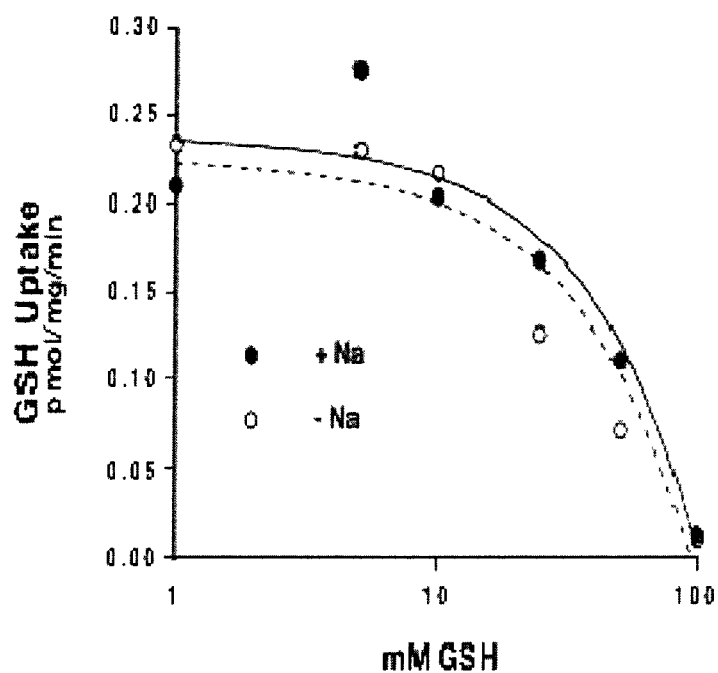
FIG. 2 is a graph of transport of radiolabeled GSH by luminal plasma membrane vesicles plotted as a function of unlabeled substrate concentration in the presence and absence of a parallel sodium gradient (50 mM). The data indicate that a carrier-mediated, sodium-independent transport process is present in the luminal plasma membrane. Similar transporters were observed in the abluminal membrane. Since an outwardly directed electrochemical gradient for GSH is normally present in cerebral capillary endothelial cells, outward leakage and cellular depletion of GSH would be expected under energy-depleted conditions when intracellular GSH is no longer synthesized.

Evidence that the Antioxidant Glutathione (GSH) is Depleted from Blood-Brain Endothelial Cells During Ischemia, and that Gamma-Glutamyl Cysteine (γ-Glu-Cys) Inhibits Cell Damage to Blood-Brain Barrier Endothelial Cells Under Conditions of Ischemia/Reperfusion GSH transport was measured in isolated luminal plasma membrane vesicles from endothelial cells of bovine brain capillaries, as described by us in the literature (56). FIG. 2 shows that passive, sodium-independent glutathione (GSH) carriers are present at the cell membrane of cerebral capillary endothelial cells that would mediate GSH depletion under energy-depleted conditions. Transport of a trace amount of radiolabeled GSH (0.2 μM) by luminal plasma membrane vesicles is plotted as a function of unlabeled substrate concentration in the presence and absence of a parallel sodium gradient (50 mM). The data indicate that a carrier-mediated, sodium-independent transport process is present in the luminal plasma membrane. Similar transporters were observed in the abluminal membrane. Since an outwardly directed electrochemical gradient for GSH is normally present in cerebral capillary endothelial cells, outward leakage and cellular depletion of GSH would be expected under energy-depleted conditions when intracellular GSH is no longer synthesized.

Cultured blood-brain barrier endothelial cells were incubated under conditions of ischemia (1.5 hours) followed by reperfusion (3.0 hours), in the presence and absence of γ-glutamyl cysteine (γ-Glu-Cys). Cellular damage was detected by measuring release of lactate dehydrogenase (LDH) into the incubation medium, following treatment.

Figure 7:
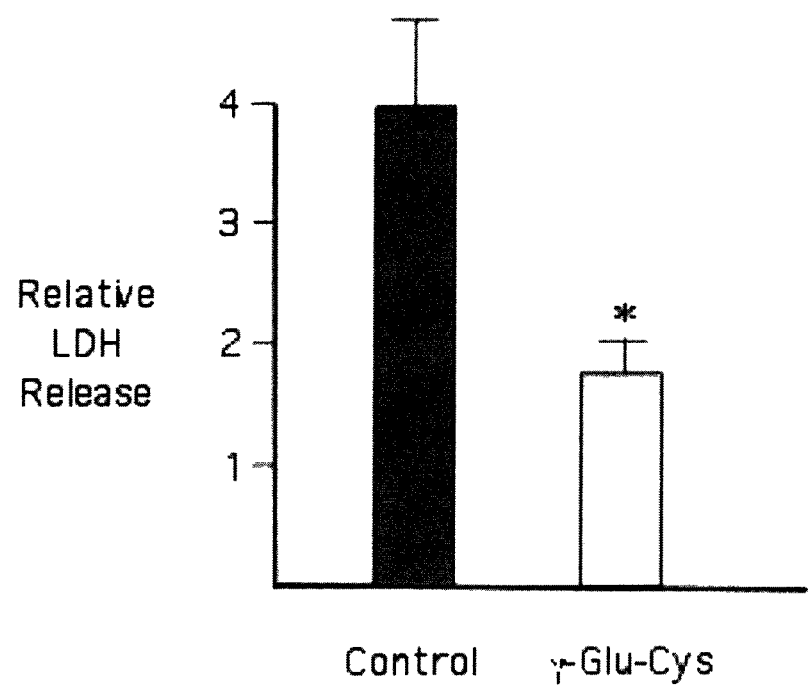
FIG. 7 is a bar graph of data showing that the antioxidant gamma-glutamyl cysteine (γ-Glu-Cys) inhibits cell damage to cerebral capillary endothelial cells cultured under conditions of ischemia and reperfusion. Lactate dehydrogenase (LDH) release is measured in cultured blood-brain barrier endothelial incubated under conditions of ischemia (1.5 hrs.) and reperfusion (3.0 hrs), in the presence and absence of γ-Glu-Cys (1 mM). γ-Glu-Cys significantly (*$P<0.05$) reduced LDH release under the experimental conditions; values are mean±SD for 3 observations.

The data show that cellular damage was significantly reduced in the presence of γ-glutamyl cysteine (γ-Glu-Cys, 1 mM) (FIG. 7) (*P<0.05). Values are mean±SD for 3 observations. The data indicate that γ-Glu-Cys is useful in preventing reperfusion injury following ischemic stroke.

Example 7

Evidence that γ-Glu-Cys and KB-R7943 Stabilize the Blood-Brain Barrier Under Conditions of Transient Stroke Rats are given transient strokes (1 hour ischemia, 24 hour reperfusion) using middle cerebral artery occlusion in the presence and absence of γ-Glu-Cys (antioxidant, 400 mg/Kg) and KB-R7943 (prevents rise in intracellular calcium concentration, 10 mg/Kg). Drugs are administered intravascularly 1 minute prior to reperfusion. The ultrastructure of blood-brain barrier endothelial cells is compared and the data from representative animals are shown in FIG. 8. The average percent change (increase) in mitochondrial area from blood-brain barrier endothelial cells in the ipsilateral cortex (stroke) compared to the contralateral internal control is significantly greater (P<0.05) when comparing animals (N=4) with the drugs, versus those without the drugs. Mitochondrial swelling is an indicator of injury and the initiation of apoptosis. The data indicate that the drugs stabilize the blood-brain barrier under conditions of transient stroke.

Example 8

Evidence that γ-Glu-Cys and KB-R7943 Reduce the Area of Infarction from Stroke

FIGS. 9a-9b are photomicrographs of coronal sections respectively from a representative stroked animal without administration of the drugs, and from a representative stroked animal with administration of the drugs, providing evidence that γ-Glu-Cys and KB-R7943 inhibit infarction in brain tissue of rats exposed to transient cerebral ischemia in vivo. Coronal sections were stained with 2,3,5-triphenyltetrazolium (TTC). FIG. 9a shows a coronal section from a stroked animal without the drugs, compared to that of a stroked animal administered the drugs, FIG. 9b. Unstained tissue observed in FIG. 9a indicates an area of infarction (arrow) in the stroked animal that was not given the drugs. The area of infarction for tissue from all 4 animals in both groups was quantified using morphometric measurements (Neurolucida), and was expressed as percent area of the stroked hemisphere. The data describing stroked animals without the drugs vs. stroked animals with the drugs, respectively, are as follows: 41.4±7.7 (mean±SE; N=4) vs. 17.3±12.2 (N=4). This difference approached significance (P=0.14) with only 4 animals in each group, and suggests that the drugs can have a general cytoprotective effect in the brain following transient ischemia.

Example 9

Evidence that γ-Glu-Cys and KB-R7943 Protect Against Neurological Deficits When Administered at the Time of Reperfusion, Following Transient Ischemia Stroked animals without drugs:
1. Right front paw deficit
2. Slow moving, with some torticolis
3. Obvious paresis
4. Obvious paresis Two additional animals died following stroke
Stroked animals with drugs
5. No observable deficits
6. No observable deficits
7. No observable deficits
8. Displays some motor deficits
No deaths following stroke Example 10

Evidence from our laboratory has shown that pretreatment with a combination of drugs, including the antioxidant γ-glutamyl-cysteine (γ-Glu-Cys), prevents ischemia-reperfusion injury to brain capillaries following simulated thrombolysis for ischemic stroke, and thus may reduce the probability of cerebral bleeding (hemorrhagic transformation). Since the drug is administered intravenously 1 min prior to thrombolysis, it must remain intact within the blood for 1 min in order to effectively reach the brain. The current study serves to confirm this. Furthermore, we have recently designed an analog of γ-Glu-Cys that we postulate will be more stable in the blood. The analog is gamma glutamyl-D-cysteine and the oxidized analog is oxidized gamma glutamyl-D-cysteine and the analog metabolite is D-cysteine.

Figure 10:
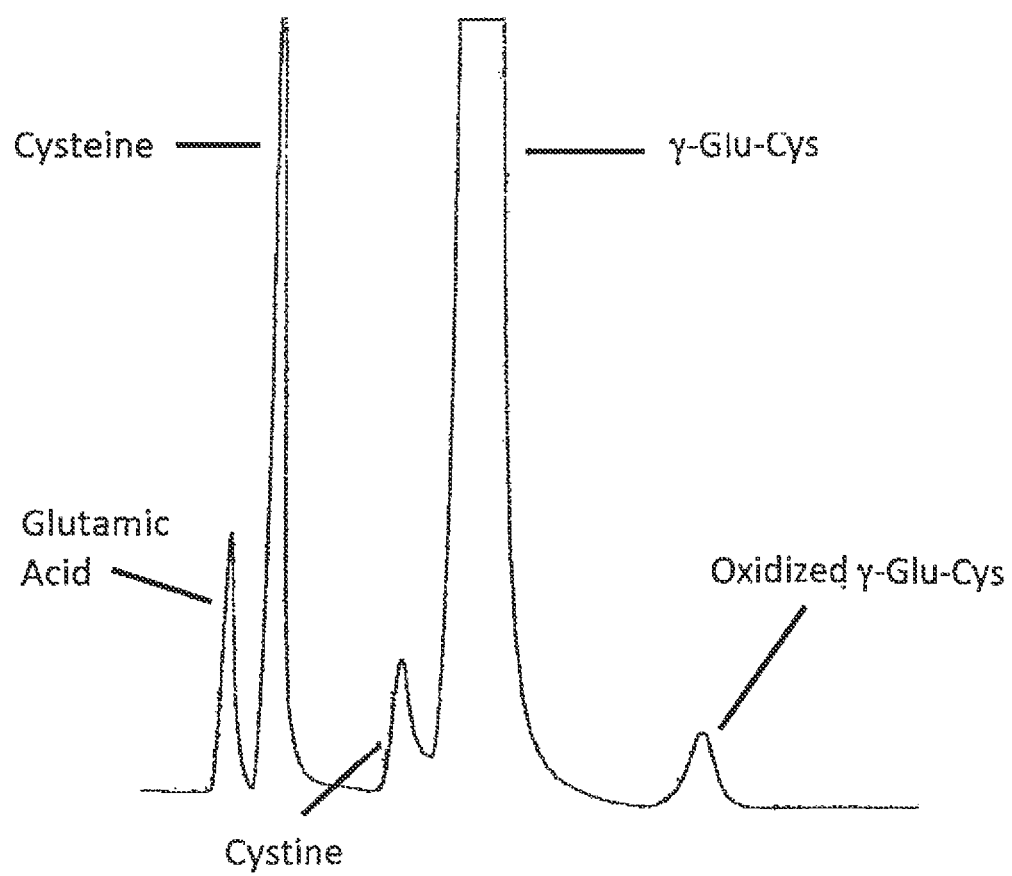
FIG. 10 shows a plot of data from high pressure liquid chromatography (HPLC) studies to identify and quantify degradative metabolites of γ-Glu-Cys. Separate peaks representing the intact peptide and its metabolites are plotted as a function of time. The area under the curve for selected peaks may be measured and compared to appropriate standards to quantify the concentration of γ-Glu-Cys and its metabolites.

The purpose of this Example is to confirm that γ-Glu-Cys remains intact within serum for at least 1 min, and to test whether our recently designed analog of γ-Glu-Cys is more stable in serum. γ-Glu-Cys and its analog (γ-Glu-D-Cys) were incubated in rat serum at a concentration of 6.25 mM for intervals of time over 180 mins, after which the presence and concentration of the peptides and metabolites were quantified by high pressure liquid chromatography (HPLC) (FIG. 10). The results show the γ-Glu-Cys had a half-life of 11.3 minutes±1.2 (N=3) SD, indicating that it remains primarily intact for 1 minute in serum. As a measure of stability, the initial velocities of degradation for γ-Glu-Cys and γ-Glu-D-Cys were compared and found to be 0.22±0.03 vs. 0.12±0.02 (mM/min), respectively. Under these conditions, the analog γ-Glu-D-Cys was more stable than the parent molecule γ-Glu-Cys (P=0.006; N=3 separate experiments). FIG. 10 shows standards representing the intact peptide and metabolites were separated using HPLC.

Figure 11:
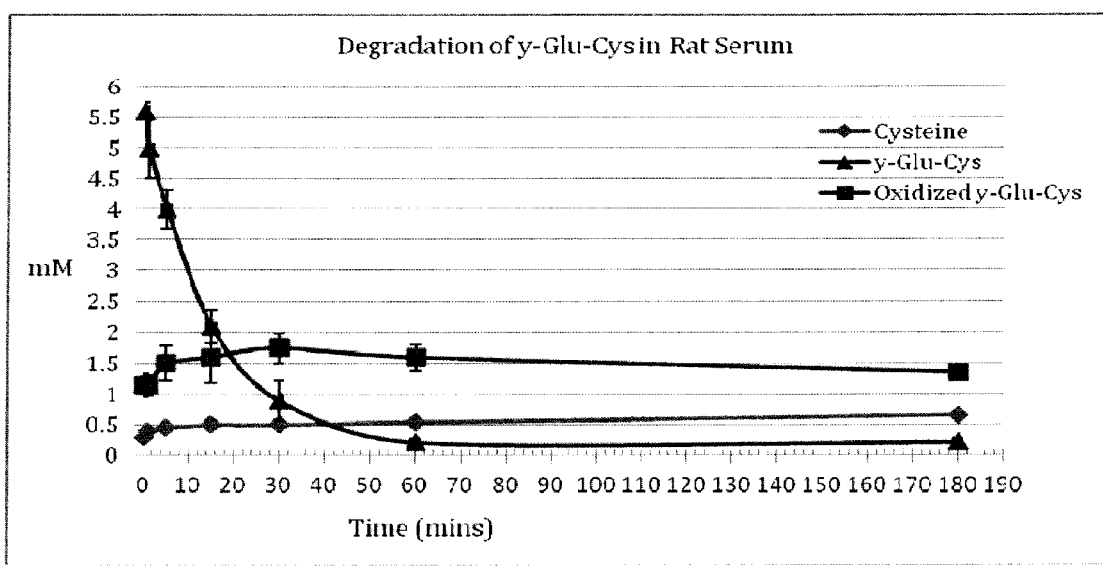
FIG. 11 shows plots mM vs. time of the degradation of γ-Glu-Cys in rat serum due to a combination of hydrolysis and oxidation. γ-Glu-Cys (6.25 mM) was incubated in rat serum at 37° C. over a period of 180 minutes. Loss of γ-Glu-Cys from the incubation medium, and the appearance of Cys and oxidized γ-Glu-Cys were quantified using HPLC to measure degradation, hydrolysis, and oxidation respectively. The ½-time for degradation of γ-Glu-Cys is 11.3±1.2 mins. Values are mean±SD. N=3 separate experiments.
Figure 12:
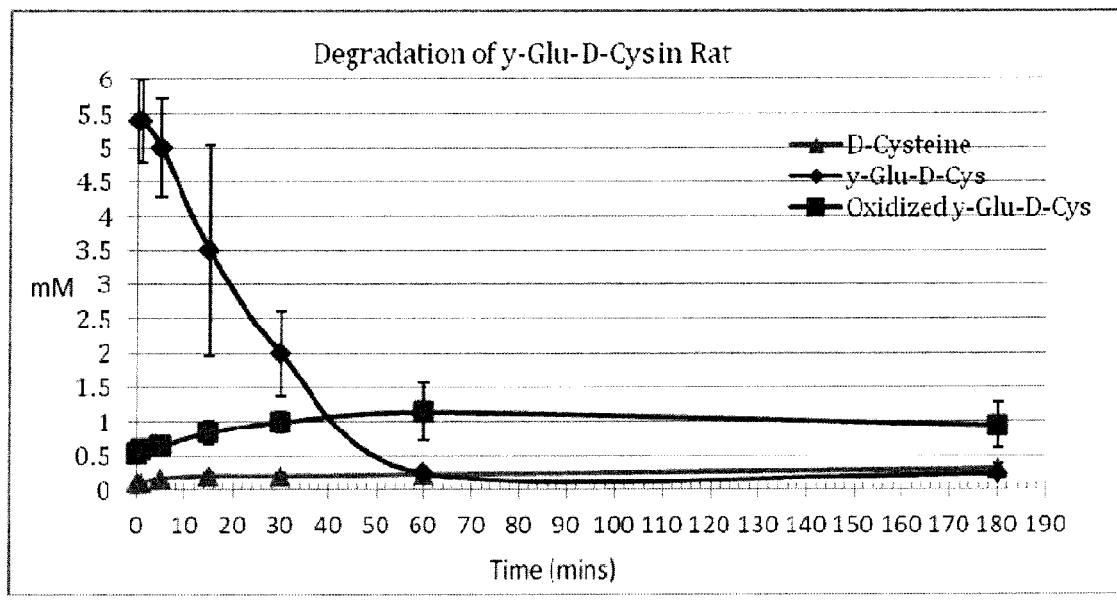
FIG. 12 shows plots mM vs. time of the degradation of γ-Glu-D-Cys in rat serum due to a combination of hydrolysis and oxidation. γ-Glu-D-Cys (6.25 mM) was incubated in rat serum at 37° C. over a period of 180 minutes. Loss of γ-Glu-D-Cys from the incubation medium, and the appearance of D-Cys and oxidized γ-Glu-D-Cys were quantified using HPLC to measure degradation, hydrolysis, and oxidation respectively. Values are mean±SD. N=3 separate experiments.
Figure 13:
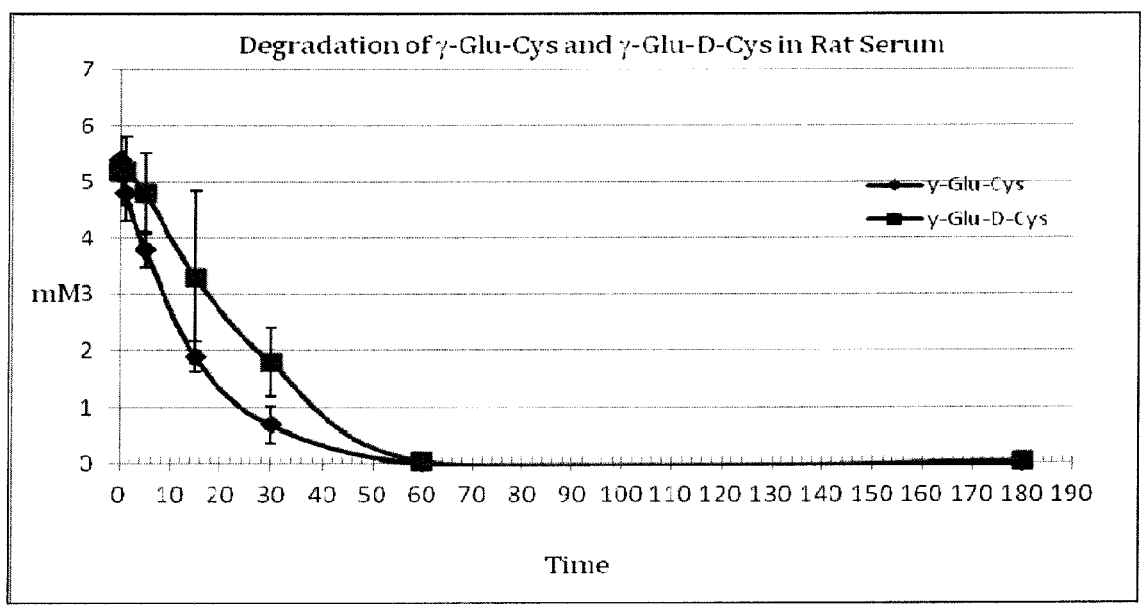
FIG. 13 shows plots mM vs. time (mins) of the degradation of γ-Glu-Cys and γ-Glu-D-Cys and indicates that γ-Glu-D-Cys is more resistant to degradation than γ-Glu-Cys when incubated in rat serum. Comparing the initial rates of degradation confirmed that γ-Glu-D-Cys is degraded more slowly (0.12±0.02 vs 0.22±0.02 mM/min, P=0.006). Values are mean±SD. N=3 separate experiments.
Figure 14:
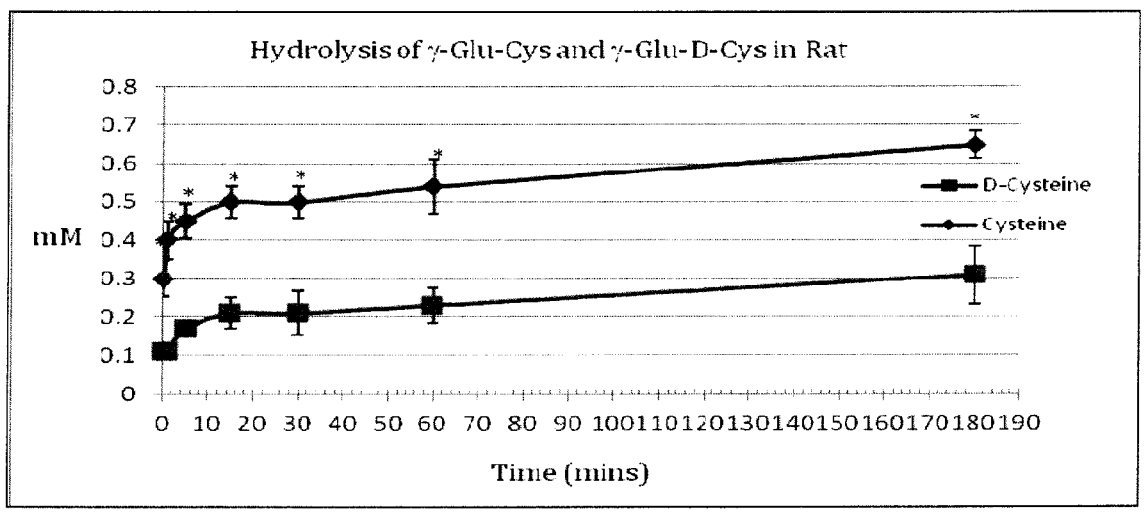
FIG. 14 shows plots mM vs. time of the hydrolysis of γ-Glu-Cys and γ-Glu-D-Cys and indicates that γ-Glu-D-Cys is more resistant to hydrolysis than γ-Glu-Cys when incubated in rat serum. Values are mean±SD. N=3 separate experiments. * indicates significant difference at P<0.05.
Figure 15:
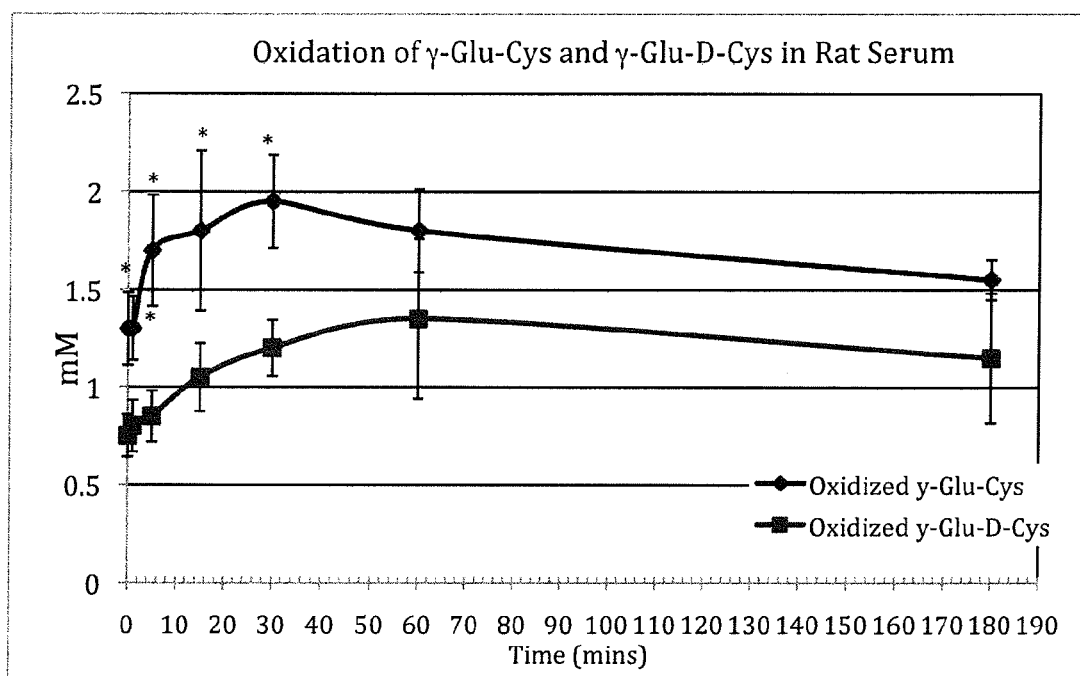
FIG. 15 shows plots mM vs. time of the oxidation of γ-Glu-Cys and γ-Glu-D-Cys and indicates that γ-Glu-Cys is initially more rapidly oxidized than γ-Glu-D-Cys when incubated in rat serum. Values are mean±SD. N=3 separate experiments. * indicates significant difference at P<0.05.

FIG. 11 is a graph showing the temporal comparison of degradation, oxidation and hydrolysis of γ-Glu-Cys. FIG. 12 is a graph showing the temporal comparison of degradation, oxidation, and hydrolysis of the analog γ-Glu-D-Cys. FIG. 13 is a graph comparing the degradation of γ-Glu-Cys and γ-Glu-D-Cys, as measured by the loss of intact peptide as a function of time of incubation. FIG. 14 is a graph comparing the hydrolysis of γ-Glu-Cys and γ-Glu-D-Cys, by appearance of cysteine and D-cysteine respectively, as a function of time. Mean±SE; * indicates significant difference at P<0.05. FIG. 15 is a graph comparing the oxidation of γ-Glu-Cys and γ-Glu-D-Cys, by appearance of oxidized γ-Glu-Cys and oxidized γ-Glu-D-Cys respectively, as a function of time. Mean±SE. * indicates P<0.05.

Figure 16A:
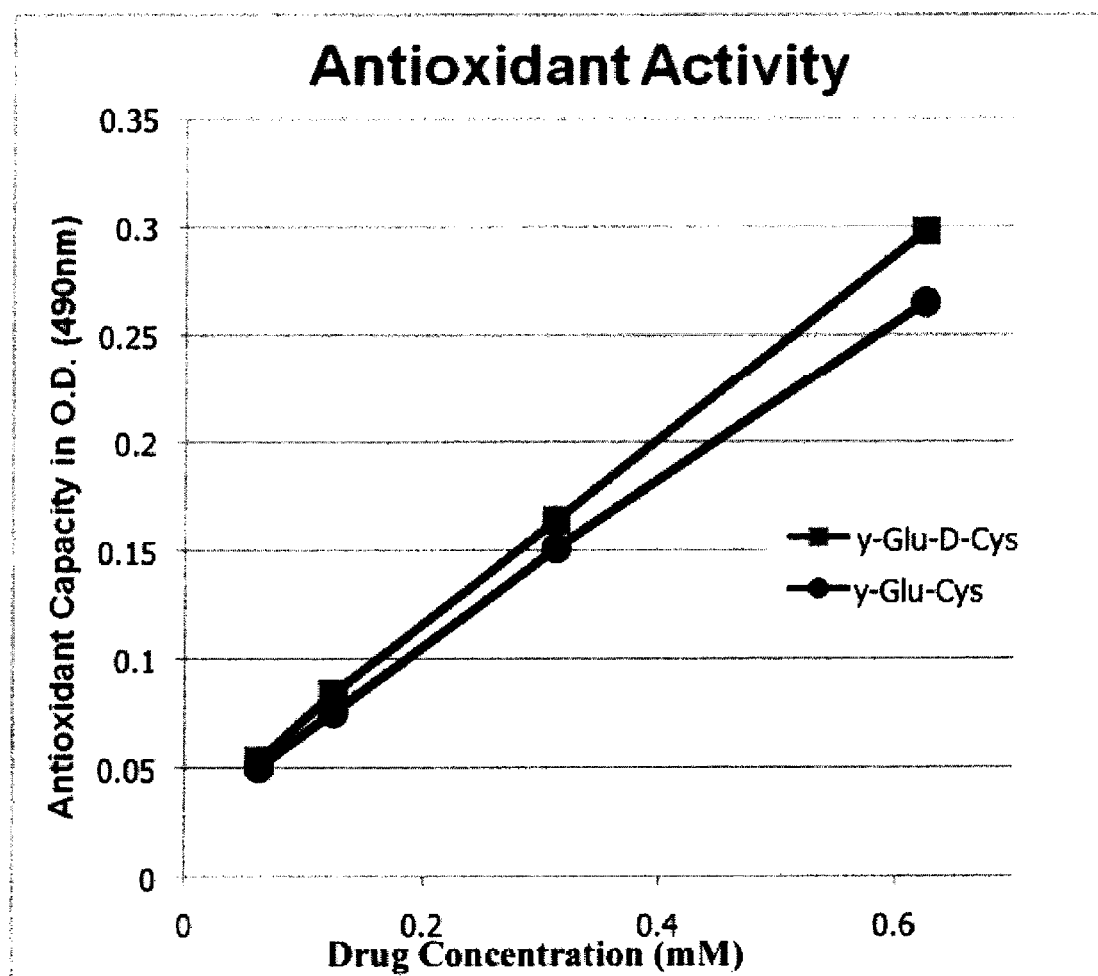
FIGS. 16a and 16b indicate that the antioxidant capacities of γ-Glu-Cys and γ-Glu-D-Cys are the same using an in vitro assay. Antioxidant capacities were measured with the Oxiselect Total Antioxidant Capacity Assay Kit, using uric acid as a standard.
Figure 16B:
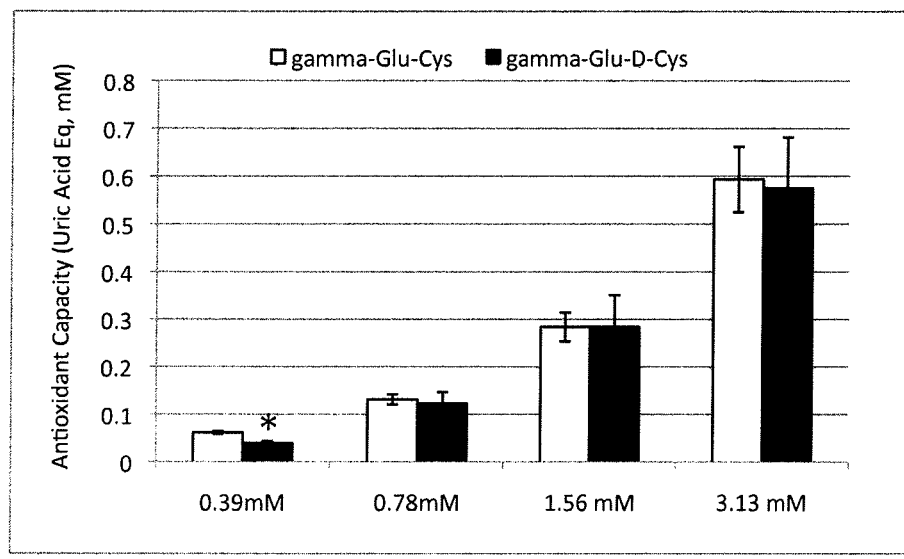

FIGS. 16a and 16b indicate that the antioxidant capacities of γ-Glu-Cys and γ-Glu-D-Cys are the same using an in vitro assay. Antioxidant capacities were measured with the Oxiselect Total Antioxidant Capacity Assay Kit, using uric acid as a standard. FIG. 16a shows the antioxidant capacities of γ-Glu-Cys and γ-Glu-D-Cys at four concentrations (0.0625, 0.125, 0.3125 and 0.625 mM) were measured in the presence of rat serum (1-9%) in Tris Buffer. The 4 values for each of these 2 plots were standardized to uric acid equivalents (mM) for a common dose, averaged, and found not to be significantly different from each other. FIG. 16b shows the antioxidant capacities of γ-Glu-Cys and γ-Glu-D-Cys at varying concentrations (0.39-3.13 mM) in human plasma (90-99%), and the antioxidant capacities were measured as described above. The data show that a marginal difference was recorded at 0.39 mM, but a significant difference was not detected between the observed antioxidant capacities at concentrations of 0.78, 1.56, and 3.13 mM. Values are mean±SE. N=3 separate experiments for the 0.78, 1.56, and 3.13 mM concentrations. N=2 separate experiments for the 0.39 mM concentration. *P=0.047.

Example 11

Figure 17:
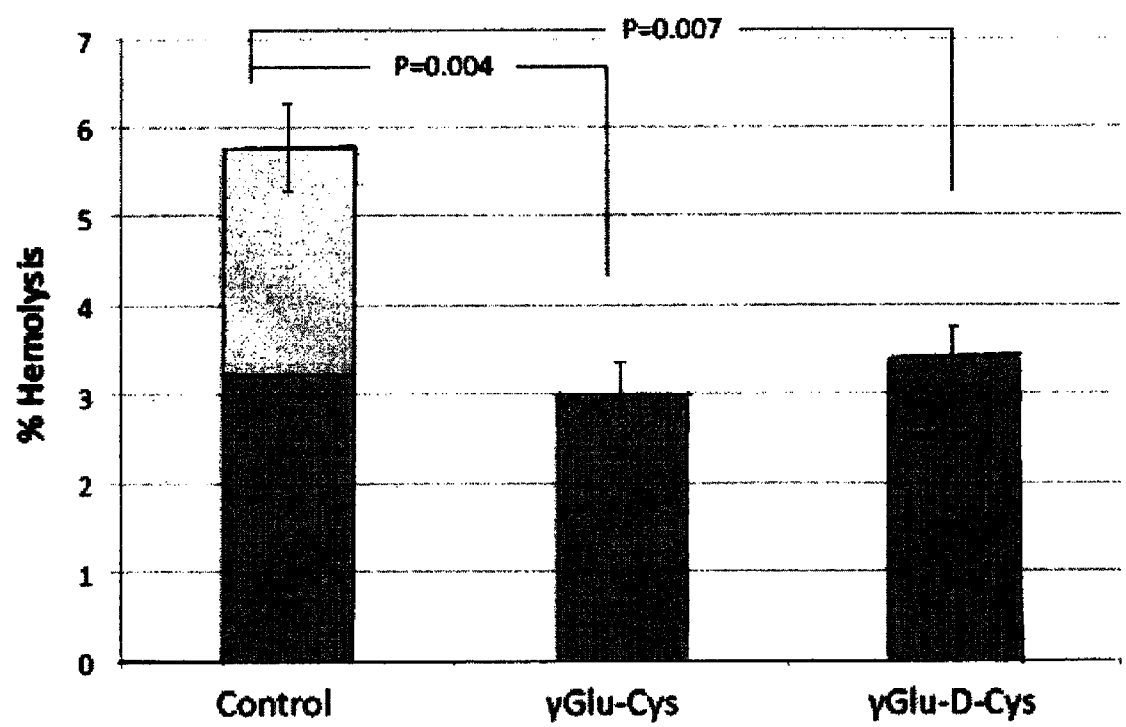
FIG. 17 is a bar graph of percent hemolysis indicating that there is no difference in the cytoprotective properties of γ-Glu-Cys and γ-Glu-D-Cys using an in vitro assay. Human red blood cells (5%) were incubated in isotonic phosphate buffer, pH 7.4 for 190 minutes at 37° C. in the presence or absence of γ-Glu-Cys and γ-Glu-D-Cys, and spontaneous hemolysis was quantified by measuring hemoglobin release spectrophotometrically at 540 nm.

FIG. 17 is a bar graph of percent hemolysis indicating that there is no difference in the cytoprotective properties of γ-Glu-Cys and γ-Glu-D-Cys using an in vitro assay. Human red blood cells (5%) were incubated in isotonic phosphate buffer, pH 7.4 for 190 minutes at 37° C. in the presence or absence of γ-Glu-Cys and γ-Glu-D-Cys, and spontaneous hemolysis was quantified by measuring hemoglobin release spectrophotometrically at 540 nm. FIG. 17 shows that both γ-Glu-Cys (1 mM) and γ-Glu-D-Cys (1 mM) significantly inhibit spontaneous hemolysis, and that there is no significant difference in their cytoprotective effect in this assay. Furthermore, since neither peptide increased hemolysis, the data suggest that both drugs are not toxic under the experimental conditions. Values are mean±SE for 4 observations.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

REFERENCES

1. The national Institute of Neurological Disorders and Stroke rt-PA Stroke Study Group. Tissue plasminogen activator for acute ischemic stroke. *N Engl J Med* 333: 1581-1587, 1995.
2. Abbruscato T J and Davis T P. Combination of hypoxia/aglycemia compromises in vitro blood-brain barrier integrity. *J Pharmacol Exp Ther* 289: 668-675, 1999.
3. Anderson M E. Glutathione and glutathione delivery compounds. In: *Advances in Pharmacology*. New York: Academic Press, 1997, p. 65-78.
4. Audus K L, Rose J M, Wang W, and Borchardt R. Brain microvessel endothelial cell culture systems. In: *Introduction to the Blood-Brain Barrier*, edited by Pardridge W M. Cambridge: Cambridge University Press, 1998, p. 86-93.
5. Betz A L, Firth J A, and Goldstein G W. Polarity of the blood-brain barrier: distribution of enzymes between the luminal and antiluminal membranes of brain capillary endothelial cells. *Brain Res* 192: 17-28, 1980.
6. Beuckmann C T and Galla H-J. Tissue culture of brain endothelial cells-induction of blood-brain barrier properties by brain factors. In: *Introduction to the blood-brain barrier*, edited by Pardridge W M. Cambridge: Cambridge University Press, 1998, p. 79-85.
7. Boado R J and Pardridge W M. A one-step procedure for isolation of poly(A)+ mRNA from isolated brain capillaries and endothelial cells in culture. *J Neurosci* 57: 2136-2139, 1991.
8. Bradbury M. *The Concept of a Blood-Brain Barrier*. New York: John Wiley and Sons, 1979.
9. Bradbury M W B. The blood-brain barrier. Transport across the cerebral endothelium. *Circ Res* 57: 213-222, 1985.
10. Choudhri T, Hoh B L, Solomon R A, Connoly E S, and Pinsky D J. Use of spectrophotometric hemoglobin assay to objectively quantify intracerebral hemorrhage in mice. *Stroke* 28: 2296-2302, 1997.
11. Cook B S, P. H. S, and Clerk A. Regulation of bcl-2 family proteins during development and in response to oxidative stress in cardiac myocytes: association with changes in mitochondrial membrane potential. *Circ Res* 85: 940-949, 1999.
12. Counillon L, Scholz W, Lang H J, and Pouyssegur J. Pharmacological characterization of stably transfected Na+/H+ antiporter isoforms using amiloride analogs and a new inhibitor exhibiting anti-ischemic properties. *Mol Pharmacol* 44: 1041-1045, 1993.
13. DeBault L E. γ-glutamyl transpeptidase induction mediated by glial foot process-to-endothelium contact in co-culture. *Brain Res* 220: 432-435, 1981.
14. DeKeyser J, Sulter G, and Luiten P G. Clinical trials with neuroprotective drugs in acute ischaemic stroke: are we doing the tight thing? *Trends Neurosci* 22: 535-540, 2001.
15. Del Zoppo G J, Von Kummer R, and Hammann G F. Ischaemic damage of brain microvessels: inherent risks for thrombolytic treatment in stroke. *J Neurol Neurosurg Psychiatry* 65: 1-9, 1998.
16. Dirnagl U, Iadecola C, and Moskowitz M A. Pathobiology of ischaemic stroke: an integrated view. *TINS* 22: 391-397, 1999.
17. Fukuhara Y and Turner R J. Sodium-dependent succinate transport in renal outer cortical brush border membrane vesicles. *Am J Physiol* 245: F374-F381, 1983.
18. Garray R P and Garrahan P J. The interaction of sodium and potassium with the sodium pumps in red cells. *J Physiol (London)* 231: 297-325, 1973.
19. Gartshore G, Patterson J, and Macrae I M. Influence of ischemia and reperfusion on the course of brain tissue swelling and blood-brain barrier permeability in a rodent model of transient focal cerebral ischemia. *Exp Neurol* 147: 353-360, 1997.
20. Greene E L and Paller M S. Calcium and free radicals in hypoxia/reoxygenation injury of renal epithelial cells. *Am J Physiol* 266: F13-F20, 1994.
21. Griffiths E J, Ocampo C J, Savage J S, Stern M D, and Silverman H S. Protective effects of low and high doses of cyclosporin A against reoxygenation injury in isolated rat cardiomyocytes are associated with differential effects on mitochondrial calcium levels. *Cell Calcium* 27: 87-95, 2000.
22. Halestrap A P. The mitochondrial permeability transition: its molecular mechanism and role in reperfusion injury. *Biochem Soc Symp* 66: 181-203, 1999.
23. Halestrap A P, Woodfield K-Y, and Connern C P. Oxidative stress, thiol reagents, and membrane potential modulate the mitochondrial permeability transition by affecting nucleotide binding to the adenine nucleotide translocase. *J Biol Chem* 272: 3346-3354, 1997.
24. Hatashita S and Hoff J T. Brain edema and cerebrovascular permeability during cerebral ischemia in rats. *Stroke* 21: 582-588, 1990.

25. Ikeda K, Nagashima T, Wu S, Yamaguchi M, and Tamaki N. The role of calcium ion in anoxia/reoxygenation damage of cultured brain capillary endothelial cells. *Acta Neuochir Suppl (Wien)* 70: 4-7, 1997.
26. Iwamoto T, Watano T, and Shigekawa M. A novel isothiourea derivative selectively inhibits the reverse mode of Na/Ca exchange in cells expressing NCX1. *J Biol Chem* 271: 22391-22397, 1996.
27. Karaki H, Ozaki H, Hori M, Mitsui-Saito M, Amano K-I, Harda K-I, Miyamoto S, Nakazawa H, Won K-J, and Sata K. Calcium movement, distribution, and functions in smooth muscle. *Pharmacol Rev* 49: 157-230, 1997.
28. Karmazyn M, Sostaric J V, and Gan X T. The myocardial Na/H exchanger. *Drugs* 61: 375-389, 2001.
29. Kuro T, Kobayashi Y, Takaoka M, and Matsumura Y. Protective effect of KB-R7943, a novel Na/Ca exchange inhibitor, on ischemic acute renal failure in rats. *J Pharmacol* 81: 247-251, 1999.
30. Kuroiwa T, Shibutani M, and Okeda R. Blood-brain barrier disruption and exacerbation of ischemic brain edema after restoration of blood flow in experimental focal cerebral ischemia. *Acta Neuropathol* 76: 62-70, 1988.
31. Ladilov Y, Haffner S, Balser-Schafer C, Maxeiner H, and Piper H M. Cardioprotective effects of KB-R7943: a novel inhibitor of the reverse mode of Na+/Ca2+ exchanger. *Am J Physiol* 276: H1868-H1876, 1999.
32. Lazdunski M, Frelin C, and Vigne P. The sodium/hydrogen exchange system in cardiac cells: its biochemical and pharmacological properties and its role in regulating internal concentrations of sodium and internal pH. *Mol Cell Cardiol* 17: 1029-1042, 1985.
33. Lee W-J, Hawkins R A, Peterson D R, and Vina J. Role of oxoproline in the regulation of neutral amino acid transport across the blood-brain barrier. *J Biol Chem* 271: 19129-19133, 1996.
34. Lee W-J, Hawkins R A, Vina J R, and Peterson D R. Glutamine transport by the blood-brain barrier: a possible mechanism for nitrogen removal. *Am J Physiol* 274: C1101-C1107, 1998.
35. Lee W-J, Peterson D R, Sukowski E J, and Hawkins R A. Glucose transport by isolated plasma membranes of the blood-brain barrier. *Am J Physiol* 272: 1997.
36. Masada T, Hua Y, Xi G, Ennis S R, and Keep R. Attenuation of ischemic brain edema and cerebrovascular injury after ischemic preconditioning in the rat. *J Cereb Blood Flow Metab* 21: 22-33, 2001.
37. Matsuda T, Arakawa N, Takuma K, Kishida Y, Kawasaki Y, Sakaue M, Takahashi K, Takahashi T, Suzuki T, and Baba A. SEA0400, a novel and selective inhibitor of the Na—Ca exchanger, attenuates reperfusion injury in the in vitro and in vivo cerebral ischemic models. *J Pharmacol Exp ther* 298: 249-256, 2001.
38. Matsui H, Homareda H, and Inoue N. Increase in Na pump activity of brain-type isoforms via increased turnover rate after glutamate excitation of cerebral neurons. In: *The sodium pump: structure mechanism, hormonal control and its role in disease*, edited by Schoner W. New York: Springer, 1994, p. 710-713.
39. Matsumoto S, Friberg H, Ferrand-Drake M, and Wieloch T. Blockade of the mitochondrial permeability transition pore diminishes infarct size in the rat after middle cerebral artery occlusion. *J Cereb Blood Flow Metab* 19: 736-741, 1999.
40. Mayer B and Oberbauer R. Mitochondrial regulation of apoptosis. *NIPS* 18: 89-94, 2003.
41. Mentzer R M. EXPEDITION: Sodium-proton exchange inhibition to prevent coronary events in acute cardiac conditions trial. *American Heart Association Scientific Sessions,* 2003.
42. Meresse S, Dehouck M-P, Delmore P, Bensaid M, Tauber J-P, Delbart C, Fruchart J-C, and Cecchelli R. Bovine brain endothelial cells express tight junctions and monoamine oxidase activity in long-term culture. *J Neurochem* 53: 1363-1371, 1989.
43. Morales A, Lachuer J, Bilbaut A, Georges B, Andrieu J-L, and Diez J. Characterization of a Na—Ca exchanger NCX1 isoform in bovine fasiculata cells of adrenal gland. *Mol Cell Biochem* 218: 41-45, 2001.
44. Muruganandam A, Smith C, Ball R, Herring T, and Stanimirovic D. Glutathione homeostasis and leukotriene-induced permeability in human blood-brain barrier endothelial cells subjected to in vitro ischemia. *Acta Neurochir Suppl* 76: 29-34, 2000.
45. Nakamura A, Harada K, Sugimoto H, Nakajima F, and Nishimura N. Effects of KB-R7943, a novel Na/Ca inhibitor, on myocardial ischemia/reperfusion injury. *Folia Pharmacol Jpn* 111: 105-115, 1998.
46. Ogata M, Iwamoto T, Tasawa N, Nishikawa M, Yamashita J, Takaoka M, and Matsumura Y. A novel and selective Na/Ca exchange inhibitor, SEA0400, improves ischemia/reperfusion-induced renal injury. *Eur J Pharmacol* 478: 187-198, 2003.
47. Orrenius S, Ankarcrona M, and Nicotera P. Mechanisms of calcium-related cell death. *Adv Neurol* 71: 137-151, 1996.
48. Peterson D R and Hawkins R A. Isolation and behavior of plasma membrane vesicles made from cerebral capillary endothelial cells. In: *Introduction to the Blood-Brain Barrier*, edited by Pardridge W. London: Cambridge University Press, 1998, p. 62-70.
49. Peterson D R and Hawkins R A. Transport studies using membrane vesicles. In: *The Blood-Brain Barrier: Biology and Research Protocols*, edited by Nag S. Totowa: Humana Press, 2003, p. 233-247.
50. Peterson D R, Rambow J, Sukowski E J, and Zikos D. Glutathione transport by the blood-brain barrier. *FASEB J* 13: A709, 1999.
51. Reese T S and Karnovsky M J. Fine structural localization of a blood-brain barrier to exogenous peroxidase. *J Cell Biol* 34: 207-217, 1967.
52. Rosenberg G A. Matrix metalloproteinases in neuroinflammation. *Glia* 39: 279-291, 2002.
53. Rosenberg G A, Estrada E Y, and J. E. D. Matrix metalloproteinases and TIMPs are associated with blood-brain barrier opening after reperfusion in rat brain. *Stroke* 29: 2189-2195, 1998.
54. Rubin L L, Hall D E, Porter S, Barbu K, Cannon C, Horner H C, Janatpour M, Liaw C W, Manning K, Morales J, Tanner L I, Tomaselli K J, and Bard F. A cell culture model of the blood-brain barrier. *J Cell Biol* 115: 1725-1735, 1991.
55. Sanchez del Pino M M, Hawkins R A, and Peterson D R. Biochemical discrimination between luminal and abluminal enzyme and transport activities of the blood-brain barrier. *J Biol Chem* 270: 14907-14912, 1995.
56. Sanchez del Pino M M, Hawkins R A, and Peterson D R. Neutral amino acid transport by the blood-brain barrier: membrane vesicle studies. *J Biol Chem* 267: 25951-25957, 1992.
57. Sanchez del Pino M M, Peterson D R, and Hawkins R A. Neutral amino acid transport characterization of iso- 58. Sebastia J, Cristofol R, Martin M, Rodriguez-Farre E, and Sanfeliu C. Evaluation of fluorescent dyes for measuring intracellular glutathione content in primary cultures of human neurons and neuroblastoma SH-SY5Y. *Cytometry* 51A: 16-25, 2003.
59. Skopicki H A, Fisher K, Zikos D, Flouret G, Bloch R, Kubillus S, and Peterson D R. Carrier-mediated transport of pyroglutamyl-histidine in renal brush border membrane vesicles. *Am J Physiol* 255: C822-C827, 1988.
60. Skopicki H A, Fisher K, Zikos D, Flouret G, and Peterson D R. Low-affinity transport of pyroglutamyl-histidine in renal brush-border membrane vesicles. *Am J Physiol* 257: C971-C975, 1989.
61. Sobolevsky A L and Khodorov B I. Blockade of NMDA channels in acutely isolated rat hippicampal neurons by the Na/Ca exchange inhibitor KB-R7943. *Neuropharmacology* 38: 1235-1242, 1999.
62. Sun D, Lytle C, and O'Donnell M. Astroglial cell-induced expression of Na—K—Cl cotransporter in brain microvascular endothelial cells. *Am J Physiol* 269: C1506-C1512, 1995.
63. Todd N V, Picozzi P, Crockard H A, and Russell R W R. Reperfusion after cerebral ischaemia: influence of duration of ischaemia. *Stroke* 17: 460-466, 1986.
64. Tsukamoto T and Nigam S K. Tight junction proteins form large complexes and associate with the cytoskeleton in an ATP depletion model for reversible junction assembly. *J Biol Chem* 272: 16133-16139, 1997.
65. Viravaidya K, Sin A, and Shuler M L. Development of a microscale cell culture analog to probe naphthalene toxicity. *Biotechnol Prog* 20: 316-323, 2004.
66. Welling L W and Grantham J J. Physical properties of isolated perfused renal tubules and tubular basement membranes. *J Clin Invest* 51: 1063-1075, 1972.
67. Wright S H, Kippen I, and Wright E M. Stoichiometry of Na+-succinate cotransport in renal brush-border membranes. *J Biol Chem* 257: 1773-1778, 1982.
68. Wulf E, Deboben A, Bautz F A, Faulstich H, and Wieland T. Fluorescent phallotoxin, a tool for the visualization of cellular actin. *Proc Natl Acad Sci USA* 76: 4498-4502, 1979.
69. Xu M, Wang Y, Hirai K, Ayub A, and Ashraf M. Calcium preconditing inhibits mitochondrial permeability transition and apoptosis. *Am J Physiol* 280: H899-H908, 2001.
70. Zhu H J and Liu G Q. Glutamate up-regulates P-glycoprotein expression in rat brain microvessel endothelial cells by an NMDA receptor-mediated mechanism. *Life Sci* 75: 1313-1322, 2004.
71. Neuwelt E, Pagel M A, Kraemer D F, Peterson D R and Muldoon L. Bone marrow chemoprotection without compromise of chemotherapy efficacy in a rat brain tumor model. *J Pharmacol Exp Ther* 309: 1-6, 2004.
72. Doolittle N D, Abrey L E, Ferrari N, Hall W A, Laws E R, McLendon R E, Muldoon L, Peereboom D, Peterson D R, Reynolds D, Senter P and Neuwelt E. Targeted delivery in primary and metastatic brain tumors. *Clin Cancer Res* 8: 1702-1709, 2002.
73. Eigel B N and Hadley R W. Antisense inhibition of Na/Ca exchange during anoxia/reoxygenation in ventricular myocytes. *Am J Physiol* 281: H2184-H2190, 2001.
74. Eigel B N, Gursahani H and Halley R W. Na/Ca exchanger plays a key role in inducing apoptosis after hypoxia in cultured guinea pig ventricular myocytes. *Am J Physiol* 287: H1466-H1475, 2004.
75. Riser B L, Kapoor S and Peterson D R. CCN genes and the kidney. In: *CCN Proteins, A New Family of Cell Growth and Differentiation Regulators*. Imperial College Press, London, 2005.
76. Peterson D R, Oparil S, Flouret G and Carone F A. Handling of angiotensin II and oxtocin by renal tubular segments perfused in vitro. *Am J Physiol* 232: F319-F324, 1977.
77. Peterson D R, Kubillus S, Binstock W and Zikos D. Effects of charge on membrane processing in the proximal nephron. *Am J Physiol* 256: C304-C309, 1989.
78. Clapham D E. TRP channels as cellular sensors. *Nature* 426: 517-524, 2003.
79. Fleig A and Penner R. The TRPM ion channel subfamily: molecular, biophysical and functional features. *Trends Pharmacol Sci* 25: 633-639, 2004.
80. Fonfria E, Marshall I C, Benham C D, Boyfield I, Brown J D, Hill K, Hughes J P, Skaper S D and McNulty S. TRPM2 channel opening in response to oxidative stress is dependent on activation of poly(ADP-ribose)polymerase. *Br J Pharmacol* 143: 515-516, 2004.
81. Harada H, Wang Y, Mishima Y, Vehara N, Makaya T and Kano T. A novel method of detecting rCBF with laser-Doppler flowmetry without cranial window through the skull for a MCAO rat model. *Brain Research Protocols* 14: 165-170, 2005.
82. O'Brien M A, Moravec R A and Reiss. Poly(ADP-ribose)polymerase cleavage monitored in situ in apoptotic cells. *Biotechniques* 30: 886-891, 2001.
83. Sehirli A O, Sener G, Satiroglu H, Ayanoglu-Dulger G. Protective effect of N-acetylcysteine on renal ischemia/reperfusion injury in the rat. *J. Nephrol* 16: 75-80, 2003.
84. Kuro T, Kobayashi Y, Takaoka M, Matsumura, Y. Protective effect of KB-R7943, a novel $Na^+/Ca^+$ exchange inhibitor, on ischemic acute renal failure in rats. *Jpn. J. Pharmacol.* 18: 247-251, 1999.
85. Warach S and Latour L L. Evidence of reperfusion injury, exacerbated by thrombolytic therapy, in human focal brain ischemia using a novel imaging marker of early blood-brain barrier disruption. Stroke 35: 2659-2661, 2004.
86. Xiaoying W, Tsuji K, Lee S-R, Ning M M, Furie K L, Buchan A M and Lo E H. Mechanisms of hemorrhagic transformation after tissue plasminogen activator reperfusion therapy for ischemic stroke. Stroke 35: 2726-2730, 2004.
87. Xu S-y and Pan, S-y. The failure of animal models of neuroprotection in acute ischemic stroke to translate to clinical efficacy. Med. Sci. Monit. Basic Res. 19: 37-45, 2013.
88. Wechsler L R. Intravenous thrombolytic therapy for acute ischemic stroke. N. Engl. J. Med. 364: 2138-46, 2011.

I claim:

1. A method for preventing blood-brain barrier reperfusion injury in a mammalian blood-brain barrier endothelial cell during reperfusion following ischemic stroke comprising administering an effective amount of a γ-glutamyl D-cysteine antioxidant to the subject.

2. The method of claim 1, wherein the mammalian blood-brain barrier endothelial cell is human cell.

3. The method of claim 1, wherein the γ-glutamyl-D-cysteine antioxidant is administered to a subject by intravenous injection into the subject.

4. The method of claim 1, wherein the γ-glutamyl-D-cysteine antioxidant is administered to a subject at a dose of about 400 mg/Kg.

5. The method of claim 1, wherein the γ-glutamyl-D-cysteine antioxidant is administered to a subject over a period of time.

6. The method of claim 5, wherein the γ-glutamyl-D-cysteine antioxidant is administered to the subject over a period of about one minute.

7. The method of claim 1, wherein the reperfusion following ischemic stroke is the result of a thrombolytic treatment.

8. The method of claim 7, wherein the thrombolytic treatment is by administering tissue plasminogen activator or urokinase.

9. The method of claim 1 further comprises administering an agent which inhibits reverse movement of Na/Ca exchange in the blood-brain barrier.

10. The method of claim 9, wherein the agent to inhibit the reverse movement of Na/Ca exchange is 2-[2-[4-(4-nitrobenzyloxy)phenyl]ethyl]isothiourea methanesulphonate (KB-R7943).

11. The method of claim 10, wherein the KB-R7943 is administered at a dose of 10 mg/Kg.

12. A kit for use in preventing blood-brain barrier reperfusion injury in a mammalian blood-brain barrier endothelial cell during reperfusion following ischemic stroke comprising an effective amount of a γ-glutamyl-D-cysteine antioxidant.

13. The kit of claim 12, wherein the blood-brain barrier endothelial cell is a human cell.

14. The kit of claim 12, wherein the effective amount is about 400 mg/Kg.

15. The kit of claim 12 further comprises an agent which inhibits reverse movement of Na/Ca exchange in the blood-brain barrier.

16. The kit of claim 15, wherein the agent to inhibit the reverse movement of Na/Ca exchange is 2-[2-[4-(4-nitrobenzyloxy)phenyl]ethyl]isothiourea methanesulphonate (KB-R7943).

17. The kit of claim 16, wherein the KB-R7943 is administered at a dose of about 10 mg/Kg.

18. A method for preventing blood-brain barrier reperfusion injury in a mammalian blood-brain barrier endothelial cell during reperfusion following ischemic stroke comprising administering an effective amount of a γ-glutamyl D-cysteine and an agent which inhibits reverse movement of Na/Ca exchange in the blood-brain barrier to the subject.

19. The method of claim 18, wherein the agent to inhibit the reverse movement of Na/Ca exchange is 2-[2-[4-(4-nitrobenzyloxy)phenyl]ethyl]isothiourea methanesulphonate (KB-R7943).

20. The method of claim 18, wherein the blood-brain barrier endothelial cell is a human cell.

21. A kit for use in preventing blood-brain barrier reperfusion injury in a mammalian blood-brain barrier endothelial cell during reperfusion following ischemic stroke comprising an effective amount of a γ-glutamyl-D-cysteine and an agent which inhibits reverse movement of Na/Ca exchange in the blood-brain barrier.

22. The kit of claim 21, wherein the agent to inhibit the reverse movement of Na/Ca exchange is 2-[2-[4-(4-nitrobenzyloxy)phenyl]ethyl]isothiourea methanesulphonate (KB-R7943).

23. The kit of claim 21, wherein in the blood-brain barrier endothelial cell is a human cell.

\* \* \* \* \*